(12) United States Patent
Chu et al.

(10) Patent No.: US 9,980,774 B2
(45) Date of Patent: May 29, 2018

(54) METHODS AND DEVICES FOR DELIVERING MICROWAVE ENERGY

(75) Inventors: Chun Yiu Chu, Fremont, CA (US);
Ketan Shroff, Pleasanton, CA (US);
Dinesh I. Mody, San Jose, CA (US);
Clarence Emmons, Capitola, CA (US);
Amrish Jayprakash Walke, Milpitas, CA (US)

(73) Assignee: MicroCube, LLC, Fremont, CA (US)

( * ) Notice: Subject to any disclaimer, the term of this patent is extended or adjusted under 35 U.S.C. 154(b) by 588 days.

(21) Appl. No.: 12/829,222

(22) Filed: Jul. 1, 2010

(65) Prior Publication Data

US 2011/0004205 A1    Jan. 6, 2011

Related U.S. Application Data

(63) Continuation-in-part of application No. 12/603,077, filed on Oct. 21, 2009, now Pat. No. 8,968,287.
(Continued)

(51) Int. Cl.
*A61B 18/04* (2006.01)
*A61B 18/18* (2006.01)
(Continued)

(52) U.S. Cl.
CPC .......... *A61B 18/18* (2013.01); *A61B 18/1815* (2013.01); *A61B 2018/00196* (2013.01); *A61B 2018/1861* (2013.01); *A61N 5/045* (2013.01)

(58) Field of Classification Search
CPC ............................. A61B 18/18; A61B 18/1815
(Continued)

(56) References Cited

U.S. PATENT DOCUMENTS 4,583,556 A   4/1986   Hines et al.
4,658,836 A   4/1987   Turner
(Continued)

FOREIGN PATENT DOCUMENTS

EP    1145686       10/2001
JP    2005-312807   11/2005
(Continued)

OTHER PUBLICATIONS

International Patent Application No. PCT/US2009/061518 filed Oct. 21, 2009 in the name of MicroCube, LLC, International Search Report and Written Opinion dated Dec. 15, 2009.
(Continued)

*Primary Examiner* — John R Downey
(74) *Attorney, Agent, or Firm* — Levine Bagade Han LLP

(57) ABSTRACT

The invention comprises novel microwave antennas wherein the microwave field profile generated by an antenna is tailored and optimized for a particular clinical application. The antennas disclosed herein incorporate one or more additional elements called shaping elements that use unique properties of microwaves such as interaction of a microwave field with one or more conductive or non-conductive elements to shape or redistribute the microwave field. Such shaping elements may be used to reduce the undesired backward coupling of the emitted microwave field to the transmission line. Such shaping elements may be used to increase the power efficiency of the antenna. The invention also discloses devices and methods for treating tissue with microwave energy emitted from the antennas for use in applications such as destroying a soil tissue by microwave ablation.

26 Claims, 14 Drawing Sheets

Related U.S. Application Data

(60) Provisional application No. 61/222,409, filed on Jul. 1, 2009, provisional application No. 61/180,133, filed on May 21, 2009, provisional application No. 61/162,241, filed on Mar. 20, 2009, provisional application No. 61/107,252, filed on Oct. 21, 2008.

(51) Int. Cl.
    *A61B 18/00* (2006.01)
    *A61N 5/04* (2006.01)

(58) Field of Classification Search
    USPC .................................. 606/33; 607/155, 156
    See application file for complete search history.

(56) References Cited

U.S. PATENT DOCUMENTS

| | | | |
|---|---|---|---|
| 4,700,716 | A | 10/1987 | Kasevich et al. |
| 5,007,437 | A | 4/1991 | Sterzer |
| 5,057,106 | A | 10/1991 | Kasevich et al. |
| 5,277,201 | A | 1/1994 | Stern |
| 5,449,380 | A | 9/1995 | Chin |
| 5,603,697 | A | 2/1997 | Grundy et al. |
| 5,741,249 | A | 4/1998 | Moss et al. |
| 5,769,880 | A | 6/1998 | Truckai et al. |
| 5,788,692 | A | 8/1998 | Campbell et al. |
| 5,861,021 | A | 1/1999 | Thome et al. |
| 5,902,251 | A | 5/1999 | vanHooydonk |
| 5,928,145 | A | 7/1999 | Ocali et al. |
| 6,287,302 | B1 * | 9/2001 | Berube ..................... 606/33 |
| 6,471,696 | B1 | 10/2002 | Berube et al. |
| 6,635,055 | B1 | 10/2003 | Cronin |
| 6,663,625 | B1 | 12/2003 | Ormsby et al. |
| 6,813,520 | B2 | 11/2004 | Truckai et al. |
| 6,817,999 | B2 | 11/2004 | Berube et al. |
| 6,929,642 | B2 | 8/2005 | Xiao et al. |
| 7,197,363 | B2 | 3/2007 | Prakesh et al. |
| 7,226,446 | B1 | 6/2007 | Mody et al. |
| 7,864,160 | B2 | 1/2011 | Geaghan et al. |
| 9,615,882 | B2 | 4/2017 | Shroff et al. |
| 2003/0057413 | A1 | 3/2003 | Kim et al. |
| 2003/0109868 | A1 | 6/2003 | Chin |
| 2003/0163128 | A1 | 8/2003 | Patil et al. |
| 2005/0240173 | A1 | 10/2005 | Palti |
| 2006/0200119 | A1 | 9/2006 | Vaska et al. |
| 2006/0293652 | A1 * | 12/2006 | van der Weide ............... 606/33 |
| 2007/0066972 | A1 | 3/2007 | Ormsby et al. |
| 2007/0139294 | A1 | 6/2007 | Dunn et al. |
| 2007/0179552 | A1 | 8/2007 | Dennis et al. |
| 2007/0203480 | A1 | 8/2007 | Mody et al. |
| 2008/0167664 | A1 | 7/2008 | Payne et al. |
| 2009/0146439 | A1 | 6/2009 | Watts |
| 2010/0121319 | A1 | 5/2010 | Chu et al. |
| 2010/0137857 | A1 | 6/2010 | Shroff et al. |
| 2010/0137860 | A1 | 6/2010 | Demarais et al. |
| 2011/0257641 | A1 | 10/2011 | Hastings |
| 2012/0116486 | A1 | 5/2012 | Naga et al. |

FOREIGN PATENT DOCUMENTS

| | | |
|---|---|---|
| WO | WO 1997/006739 | 2/1997 |
| WO | WO 2003/053259 | 7/2003 |
| WO | WO 2003/088858 | 10/2003 |
| WO | WO 2006/004585 | 1/2006 |
| WO | WO 2009/146439 | 12/2009 |
| WO | WO 2010/048334 | 4/2010 |
| WO | WO 2010/048335 | 4/2010 |
| WO | WO 2012/003232 | 1/2012 |
| WO | WO 2013/149245 | 10/2013 |

OTHER PUBLICATIONS

International Patent Application No. PCT/US2009/061547 filed Oct. 21, 2008 in the name of MicroCube, LLC, International Search Report and Written Opinion dated Dec. 11. 2009.
International Patent Application No. PCT/US2009/061548 filed Oct. 21, 2009 in the name of MicroCube, LLC, International Search Report and Written Opinion dated Dec. 11, 2009.
U.S. Appl. No. 12/603,134, filed Oct. 21, 2009.
U.S. Appl. No. 14/462,434, filed Aug. 18, 2014.
U.S. Appl. No. 12/603,349, filed Oct. 21, 2009.
U.S. Appl. No. 12/603,077, filed Oct. 21, 2009.
U.S. Appl. No. 14/635,980, filed Mar. 2, 2015.

\* cited by examiner

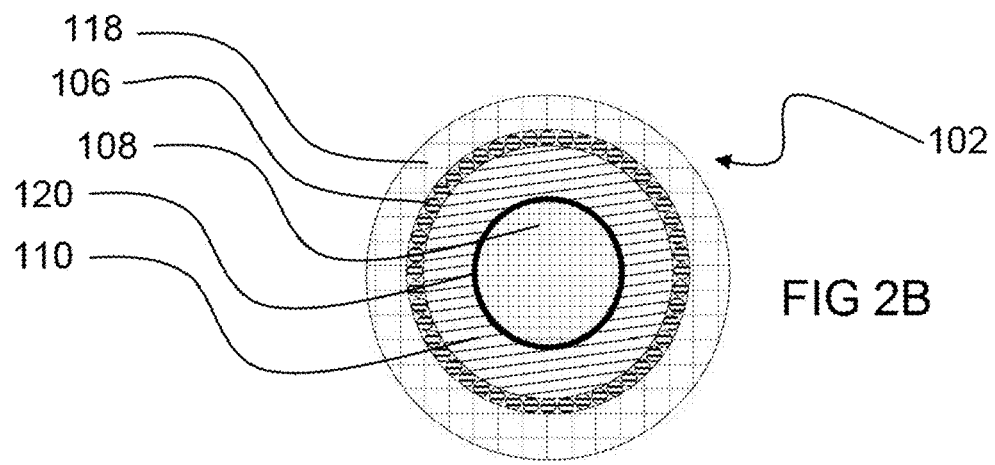
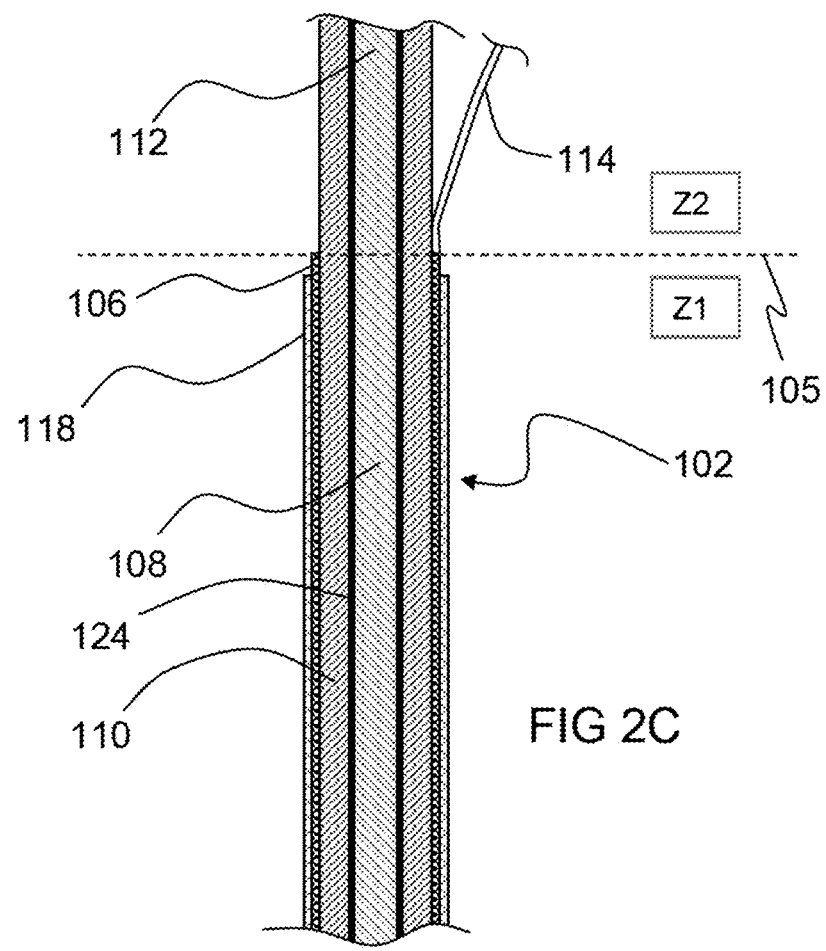

FIG 4B    105  105    FIG 4C

METHODS AND DEVICES FOR DELIVERING MICROWAVE ENERGY

CROSS-REFERENCE TO RELATED APPLICATIONS

This application claims the benefit of U.S. Provisional Patent Application No. 61/222.409, filed on Jul. 1, 2009 and is a continuation-in-part of U.S. patent application Ser. No. 12/603,077, filed on Oct. 21, 2009, the contents of which is incorporated herein by reference in their entireties. U.S. patent application Ser. No. 12/603,077 also claims the benefit of U.S. Provisional Patent Application No. 61/222,409, filed on Jul. 1, 2009, 61/180,133 filed May. 21, 2009, 61/162,241 filed Mar. 20, 2009 and 61/107,252 filed Oct. 21. 2008.

FIELD OF THE INVENTION

This invention relates to microwave antennas and devices incorporating such antennas usable for performing diagnostic and/or therapeutic procedures on or within a patient's body.

BACKGROUND OF THE INVENTION

Microwaves antennas are used in a variety of medical devices to treat several medical conditions. Several conditions including cardiac electrophysiological disorders, cancer, Menorrhagia, etc. are currently treated by applying microwave energy for ablating tissue. For example, microwave antennas (e.g. helical antennas) have been used in medical applications including treatment of benign prostate hyperplasia, cancer treatment, etc. Many of the existing antennas have common disadvantages such as device shaft heating and non-uniform lesion profile along the length of the antenna.

FIG. 1B illustrates some of the common disadvantages of prior art antennas used for ablating solid tissue such as solid tumors. Devices that use microwave ablation for treating tumors are advantageous over devices that use other ablation modalities because of their potential to create relatively larger, uniform volumetric lesions that are relatively unaffected by the heat sink effect of a nearby blood vessel. Most existing microwave ablation devices are derived from known microwave antenna structures such as monopole or dipole or helical antenna and have a linear structure. Their SAR and thermal profile are substantially elliptical and they are approximately similar to the shape of a football as shown in FIG. 1B. FIG. 1B shows a photograph of the cut surface of swine liver that was ablated using a monopole microwave antenna. FIG. 1B shows an elliptical ablation wherein only a portion of the ablation extended over a microwave antenna 104 (zone Z2) and a significant portion of the ablation extended over the shaft of the transmission line 102 (zone Z1). A significant amount of microwave field is located proximal to the distal end of the coaxial cable or other transmission line feeding the radiating element (monopole antenna). Such an ablation shape is caused due to the undesired backward coupling of the microwave field emitted by the antenna to the distal region of a conductor of the transmission line (e.g. the outer conductor of a coaxial cable). This causes a significant portion of the microwave field to be located around the distal region of the transmission line as a "long tail" instead of being localized around the microwave antenna. This portion of the microwave field can damage healthy tissue and increase the morbidity of the medical procedure. Further, this portion of the microwave field can heat up the transmission line and further damage healthy tissue. In order to overcome this problem, microwave devices have been developed that comprise a cooling mechanism around the transmission line. However, this increases the outer diameter of the device thereby increasing the invasiveness of the procedure. Further, devices with a cooling mechanism need extra equipment for circulating the coolant through the cooling mechanism thereby increasing the device complexity and cost.

Referring again back to FIG. 1B, it is clear that the backward coupling causes only a fraction of the microwave field to be delivered to the target tissue. A large portion of the field is located over non-target tissue and is thus wasted. This reduces the efficiency of the antenna. Antennas with lower efficiency need a higher power setting and/or a longer energy delivery time setting to achieve the same clinical action. Higher power delivery requires the use of larger diameter transmission lines which in turn increases the invasiveness of the procedure. Prior art antennas have tried to use various additional elements located on the microwave device to cut backward coupling. Examples of such elements are chokes, floating sleeves, triaxial construction and baluns. However, such elements are located on the outer surface of the transmission line and thus increase the size of the transmission line. This in turn increases the invasiveness of the procedure.

Also, it is difficult to use a single existing microwave antenna such as a single monopole antenna to ablate tumors that have a thickness or diameter of a few centimeters in a sufficiently short time. For many cancer-related applications, the targeted tumors have an excessive size (e.g. diameter of several centimeters) and a single monopole antenna is of limited use. One of the solutions proposed to increase the lesion size involves using multiple ablation devices simultaneously. This increases the complexity of the ablation system. The overall size and cost of the ablation device is also increased due to more number of elements employed in the system. Also, this increases the invasiveness and complexity of the procedure. Another option to increase the lesion size is to increase the microwave power delivered through the antenna. However, this may increase the temperature of the transmission line of the antenna to unsafe levels thereby increasing the risk of damaging healthy tissue.

Thus there is a need for more efficient microwave antennas that are capable of generating uniquely shaped microwave fields that overcome these problems.

SUMMARY OF THE INVENTION

Several medical applications of the invention for applying energy such as microwave energy to target materials such as tissue are disclosed herein. Energy may be applied to tissue to achieve a variety of clinically useful effects. Examples of such effects include, but are not limited to: 1. ablating tissue to kill or otherwise damage tissue, 2. causing heat-induced modification of tissue (e.g. heat shrinkage of collagen), 3. causing heat-induced modification of an artificially introduced material (e.g. heat induced polymerization of an injected monomer), 4. warming tissue to change the metabolic activity of tissue (e.g. warming tissue to increase the metabolism), 5. causing fat liquefaction e.g. to ease fat extraction during Microwave Assisted Lipoplasty, 6. causing controlled tissue death to debulk tissue for treating conditions such as Obstructive Sleep Apnea, BPH, etc., 7. delivering energy to tissue to change the electrophysiological characteristics of that tissue, and 8. increasing the efficacy of a therapy (e.g. chemotherapy) in a local region of tissue.

The present invention discloses devices and methods for treating tissue with microwave energy. In several method embodiments, microwave energy is used for ablating tissue e.g. for treating atrial fibrillation by controlled ablation of left atrial tissue, etc.

The device and methods disclosed herein may be used with or without modifications to create one or more point, linear, area or volumetric lesions. The present invention discloses various embodiments of flexible, low-profile devices that can be inserted non-invasively or minimally invasively into or near the target tissue.

Some of the embodiments herein may be broadly described as microwave devices comprising a transmission line such as a coaxial cable and an antenna connected to the coaxial cable. The antenna comprises 1. a radiating element, 2. one or more shaping elements and 3. one or more antenna dielectrics covering one or more portions of the radiating element and/or the shaping element. In embodiments wherein transmission line is a coaxial cable, the radiating element may be a continuation of the inner conductor of the coaxial cable or may be an additional conductive element electrically connected to the inner conductor of the coaxial cable. The radiating element radiates a microwave field that is characteristic of its specific design. The radiated microwave field causes agitation of polarized molecules, such as water molecules, that are within target tissue. This agitation of polarized molecules generates frictional heat, which in turn raises the temperature of the target tissue. Further, the microwave field radiated by the radiating element may be shaped or otherwise redistributed by one or more shaping element(s) in the antenna. In one embodiment, the shaping element(s) are made of an electrically conductive material (e.g. one or more metallic objects of various sizes, shapes, orientations, etc.). In this embodiment, the shaping element(s) may be electrically connected to the outer conductor or shielding element of the transmission line (e.g. the outer conductor of a coaxial cable). In an alternate embodiment, the shaping element(s) are not in direct electrical conduction with the outer conductor or shielding element of the transmission line e.g. the outer conductor of a coaxial cable. The one or more antenna dielectrics may cover one or more portions of one or both of: radiating element and shaping element. The antenna dielectrics may be used for changing the propagation of the microwave field from one or both of: radiating element and shaping element to the surrounding. The antenna dielectrics may be used for changing the matching of the antenna.

The one or more additional shaping elements in the antenna may be used to create a more uniform microwave field distributed over a larger region. The one or more shaping elements in the antenna may also be used to improve the power deposition by the antenna. This may be achieved by redistributing the field such that a significant majority of the microwave field is located around the microwave antenna and an insignificant portion of the microwave field is located around the distal region of the transmission line. One or both of radiating element and shaping element may be enclosed in an antenna dielectric material In several of the embodiments disclosed herein, a conductive element (e.g. a length of metallic wire) electrically connected to the outer conductor of a coaxial cable is used to shape the microwave field. The one or more shaping elements may be used to prevent the microwave field from coupling backwards to the distal region of the transmission line. The one or more shaping elements may be used to prevent or substantially reduce the microwave field from heating the distal region of the transmission line.

The one or more additional shaping elements in the antenna may be used to improve the impedance matching of the antenna. This in turn reduces the standing wave along the transmission line which in turn reduces the undesired heating of the transmission line by the standing wave.

The use of one or more shaping elements allows the purposeful designing of antennas that can be tailored to a specific clinical application. Thus a microwave antenna designer is no longer restricted to using only the existing linear antenna geometries. Rather, he has the freedom to use the most suitable geometry (e.g. linear, non-linear planar, 3-dimensional, etc.) that is best suited for the specific clinical application.

Several embodiments of radiating elements and shaping elements and combinations thereof are described herein. The shapes of the cross section of radiating element and shaping element may be designed to achieve the desired mechanical and microwave properties. Examples of such cross section shapes include, but are not limited to round, oval, rectangular, triangular, elliptical, square, etc. Various antennas may be designed using a combination of a radiating element disclosed herein and a shaping element disclosed herein. The shape of the microwave field emitted by such antennas can be purposely shaped by designing the antenna. For example, an antenna may be designed to generate a microwave field designed to create a deeper ablation in the center of a target organ and shallower ablation towards the periphery of the target organ.

Various embodiments of antenna 104 may be designed to generate a variety of shapes of SAR and/or the ablation profile. For example, antennas 104 may be designed to generate substantially square, triangular, pentagonal, rectangular, round or part round (e.g. half round, quarter round, etc.), spindle-shaped or oval SARs or ablation patterns.

The methods and devices disclosed herein e.g. (a linear antenna 104 disclosed herein) may be navigated through the anatomy and positioned at one or more positions within the target anatomy using one or more steerable or non-steerable devices. Any of the antennas disclosed herein may comprise one or more attachments or integral elements to enable the user to navigate the antenna through the anatomy. Examples of such attachments or elements include, but are not limited to: integral tethers or external pull wires to pull one or more regions of a device or to bend or deflect one or more regions of a device, internal pull wires adapted to bend or deflect one or more regions of a device, one or more elements adapted to be steered by a surgical magnetic navigation modality, etc. Examples of such steerable systems are disclosed in U.S. Pat. No. 7,736,360, US Patent Publication No. 2008-0188850 and US Patent Publication No. 2010-0016784, the entire disclosures of which are incorporate herein by reference.

The antennas disclosed herein may be deployed from an insertion configuration to a working configuration before being placed in the vicinity or inside of the target tissue. Alternately, the antennas may be deployed from an insertion configuration to a working configuration after being placed in the vicinity or inside of the target tissue. The deployment of the antennas disclosed herein may be done by one of several methods. The antennas herein may be navigated to the target tissue in a fully deployed configuration. In one embodiment, an antenna is navigated to the surface of an abdominal organ e.g. the liver in a fully deployed configuration through a laparotomy. In another embodiment, an antenna disclosed herein is deployed through an introducer or sheath in which the antenna is in a collapsed, low-profile configuration when inside the introducer and is deployed to a working configuration after the antenna exits the introducer. The antenna may be deployed after the antenna exits the introducer by one or more of: the elastic property of the antenna or its components, the super-elastic property of the antenna or its components, the shape memory property of the antenna or its components, use of a mechanical deployment mechanism for the antenna or its components, use of one or more anatomical regions to change the shape of one or more antenna portions, etc. One or more portions of the antennas herein may be malleable or plastically deformable. This allows the user to shape an antenna to ensure better contact with target tissue or better navigation through the anatomy.

The devices disclosed herein comprise antennas wherein the ablation profile generated by an antenna is tailored and optimized for a particular clinical application. For example, in the embodiments wherein a microwave antenna is used to ablate the entire cavity wall or an entire circumferential region of the cavity wall, the ablation profile may be designed to ablate substantially the entire cavity wall or an entire circumferential region of the cavity wall without the need for repositioning of the antenna. In such embodiments, the microwave field may circumferentially envelop the entire antenna. For example, in the embodiments wherein a microwave antenna is used to ablate a tissue volume, the ablation profile may be designed to ablate substantially the entire tissue volume without requiring repositioning of the antenna. In several device embodiments herein, microwave antennas are designed such that they ablate a substantially linear region of tissue. Several such linear lesions may be created to form a lesion pattern that achieves the desired clinical result.

The antennas disclosed herein may be conformable to acquire the shape of a portion of the target anatomy or otherwise be shaped by one or more portions of the target anatomy. For example, the antennas disclosed herein may be elastically flexible to conform to the shape of a small cavity or to the shape of an adjacent wall of the cavity into which the antenna is deployed. The antennas disclosed herein may be sized and shaped to approximate the size and shape of the target anatomy such as the uterine cavity.

Several embodiments of slim and flexible ablation devices are disclosed herein. This allows the user to introduce such ablation devices minimally invasively through small incisions or openings or even non-invasively through natural openings or passageways. Examples of minimally invasive introduction includes percutaneous introduction through the vasculature. Examples of non-invasive introduction includes introduction from the anus, mouth or nostrils into the gastro-intestinal tract, introduction from the vagina into the female reproductive system, introduction from the urethra into the urinary system, introduction from the ear, nostrils or mouth into the ENT system, etc. The devices and methods disclosed herein may be used to ablate diseased tissue or healthy tissue or unwanted tissue in organs or artificially created cavities. The devices disclosed herein may be introduced through laparoscopic, thoracoscopic, cystoscopic, hysteroscopic or other endoscopic openings or instrumentation into or near organs or bodily cavities. The methods disclosed herein may be performed under real-time monitoring e.g. by using one or more of: direct visual observation, hysteroscopy, cystoscopy, endoscopy, laparoscopy, ultrasound imaging, radiological imaging, etc.

Various additional features may be added to the devices disclosed herein to confer additional properties to the devices disclosed herein. Examples of such features include, but are not limited to one or more lumens, ability to apply a vacuum or suction to the target anatomy, ability to visualize one or more regions of the target anatomy, ability to limit the depth of insertion into the target anatomy, ability to deploy the antenna, ability to connect to a source of energy, etc.

Several of the method and device embodiments are designed to minimize the use of anesthesia such that the methods may potentially be performed using only local anesthesia.

The dimensions or other working parameters of the devices disclosed herein may be adjustable or programmable based on user inputs. The user input may be based on factors such as patient's anatomical data including anatomical dimensions and the desired level of safety and efficacy.

The various microwave antennas and the microwave engineering principles disclosed herein (e.g. the use of a shaping element to shape the field, the use of a shaping element to reduce backward coupling, the use of a shaping element to increase power deposition, etc.) may be also used in a variety of non-medical applications. The near field of the microwave antennas disclosed herein may be used on target materials, such as food, industrial products, semiconductors, etc. The near field of the microwave antennas disclosed herein may be used for cooking or heating foods, in industrial processes for drying and curing products, in semiconductor processing techniques to generate plasma for processes such as reactive ion etching and plasma-enhanced chemical vapor deposition (PECVD). The near and/or far field of such antennas may be used in short or long range communication systems including, but not limited to: wireless local area networks, long distance microwave communication, satellite communication, cellular phone communication, etc.

BRIEF DESCRIPTION OF THE DRAWINGS

FIG. 2B shows a section through an embodiment of a coaxial cable usable for the ablation device of FIG. 2A and for other ablation devices disclosed herein.

FIG. 2C shows a longitudinal section of the embodiment of the ablation device of FIG. 2A through the distal end of a coaxial cable.

FIGS. 4B and 4C show the front and side views respectively of the SAR profile generated by an antenna with a center loop similar to the antenna of FIG. 4A.

DESCRIPTION OF THE INVENTION

Figure 1A:
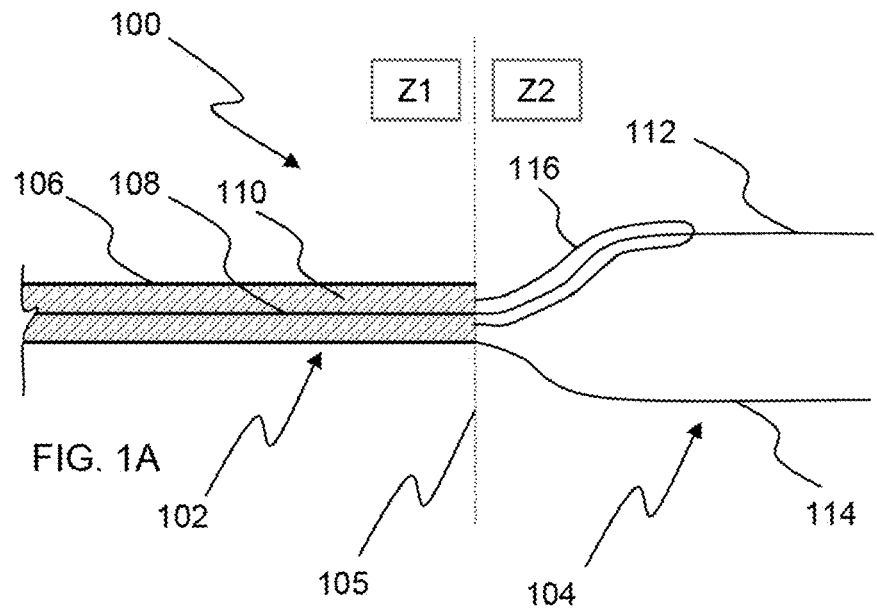
FIG. 1A shows a schematic view of an embodiment of a microwave ablation device of the present invention having a microwave antenna comprising a radiating element and a microwave field shaping element.

This specification discloses multiple antenna designs, systems, structures and devices, and associated methods, which illustrate various aspects of the invention. While these systems, structures and devices, and associated methods, are discussed primarily in terms of some particular clinical applications (e.g. ablating cardiac tissue to treat arrhythmias, endometrial ablation), the methods and devices disclosed herein are applicable for use in other bodily structures, as well. These systems, structures and devices, and associated methods, may be used for ablating tissue in, or adjacent to, the brain, prostate gland, portions of the urinary tract, gall bladder, uterus and other portions of the female reproductive tract, regions of the vasculature, intestines and other portions of the lower alimentary tract, stomach and other portions of the upper alimentary tract, liver and other digestive organs, lungs, skin, mucus membranes, kidneys, reproductive organs, joints, or other organs or soft tissues of the body. The devices and methods disclosed herein may be used for the treatment of knee disorders, anterior cruciate ligament instability, vertebral disk injuries and chronic low back pain. The devices and methods disclosed herein may be used several arthroscopic applications such as shrinking the tissues of the ligamentous joint capsule to increase the tension on these ligaments for stabilizing the shoulder joint.

Several devices and methods disclosed herein may be used to treat tissue by microwave thermal ablation. Even though a significant portion of the disclosure is about microwave device and methods for ablation of tissue to kill or otherwise damage tissue, microwave energy may be applied to tissue to achieve a variety of clinically useful effects other than ablation. Examples of such effects include, but are not limited to: 1. causing heat-induced modification of tissue (e.g. heat shrinkage or other alteration in the properties of collagen), 2. causing heat-induced modification of an artificially introduced material (e.g. heat induced polymerization of an injected monomer), 3. warming tissue to change the metabolic activity of tissue (e.g. warming tissue to increase metabolism), 4. causing fat liquefaction e.g. to ease fat extraction during Microwave Assisted Lipoplasty, 5. causing controlled tissue death to debulk tissue for treating conditions such as Obstructive Sleep Apnea, 6. delivering energy to tissue to change the electrophysiological characteristics of that tissue, and 7. increasing the efficacy of a therapy (e.g. chemotherapy) in a local region of tissue. Even though several microwave emitting device embodiments herein are called ablation devices 100, such microwave emitting device embodiments may be used for methods that do not involve ablation of tissue.

Microwave thermal ablation does not depend on the conduction of electricity to tissue unlike RF ablation. Thus, devices using microwave thermal ablation such as the devices disclosed herein don't need good contact with tissue. They can function well even without perfect contact with the target tissue. Thus, the devices disclosed herein do not require extremely precise placement in tissue, thereby reducing the dependence of procedure outcome on physician skills. The devices herein are designed to have a distal microwave emitting portion comprising an antenna and a proximal shaft. The proximal shaft comprises a transmission line such as a flexible coaxial cable that delivers microwave energy from a microwave generator to the microwave emitting portion. The shaft can be designed to be slim (e.g. <3 mm in diameter) to enable the introduction of the ablation device through narrow openings. The shaft can be designed to be flexible such that minimal forces are exerted on bodily tissues during the introduction of the ablation devices into the anatomy. The flexible nature of the shaft enables the shaft to take the natural shape of passage during introduction instead of distorting the passage by the shaft of the device. For example, when a device is introduced trans-cervically into the uterus, the shaft may acquire the shape of introduction passage comprising the vagina, cervical canal and uterine cavity instead of distorting one or more of the vagina, cervical canal and uterine cavity. The designs of the coaxial cables disclosed herein confer sufficient flexibility to the device shaft such that the device shaft is capable of bending by more than 45 degrees when it experiences distorting forces by the anatomy. If desired, the device shaft may be made stiffer by adding one or more coatings, coverings, stylets and other stiffening elements.

Several of the experiments and simulations herein were performed at 0.915 GHz or 2.45 GHz ISM band. Antennas, methods, etc. disclosed herein may be used with or without modifications at other frequencies including, but not limited to ISM bands of 0.433 GHz, 5.8 GHz, etc. The microwave power generator may be magnetron based or solid state. The microwave power generator may be single or multi-channel. The microwave power generator used for the experiments comprised a Vector Network Analyzer (Agilent 8753 series) and amplifier modules build in-house using transistors from Freescale Semiconductor (Austin, Tex.). The power measurement was made using a power meter (ML2438A Power Meter, Anritsu Company, Richardson, Tex.). Similar devices and components can be used to design the microwave generator for clinical use with the devices and methods disclosed herein.

In the experiments, where desired, a fiber optic thermometry system (FOT Lab Kit by LumaSense Technologies, Santa Clara, Calif.) was used to measure the temperature at several locations in the tissue. The fiber optic thermometry system was used since it has no metallic components that might interfere with the microwave field. Similar non-interfering thermometry may be used to measure the temperature at one or more locations during an ablation procedure.

FIG. 1A shows a schematic view of an embodiment of a microwave ablation device of the present invention having a microwave antenna comprising a radiating element and a microwave field shaping element. This schematic view demonstrates the general design principles in some of the antenna embodiments disclosed herein. In FIG. 1A, microwave ablation device 100 comprises a transmission line such as a coaxial cable 102. An antenna 104 is connected to the distal end of coaxial cable 102. FIG. 1A shows microwave ablation device 100 divided into a first zone Z1 and a second zone Z2 by an imaginary transition line 105. First zone Z1 is proximal to second zone Z2. Transition line 105 is defined by the distal end of coaxial cable 102 and is substantially perpendicular to the axis of coaxial cable 102 at the distal end of coaxial cable 102. In the embodiment shown in FIG. 1A, the distal region of coaxial cable 102 lies entirely within first zone Z1 and antenna 104 lies entirely within second zone Z2. In a one embodiment, a single microwave signal is fed to antenna 104 through coaxial cable 102. Antenna 104 generates a microwave field. The near field of the microwave field generated by antenna 104 may be used for tissue ablation.

In FIG. 1A, antenna 104 comprises a radiating element 112 and a shaping element 114. Radiating element 112 may be made of a variety of conducting materials e.g. metals, conductive polymers, materials with embedded conductive particles, etc. When microwave energy is delivered through coaxial cable 102 to antenna 104, a first microwave field is emitted by radiating element 112. The first microwave field interacts with shaping element 114. This interaction induces a leakage current on shaping element 114. The leakage current in turn creates a second microwave field. The first microwave field and the second microwave field together combine to produce a unique shaped microwave field of antenna 104 that is clinically more useful that the unshaped microwave field generated by an antenna 104 comprising only radiating element 112. Thus the original microwave field is redistributed by the design of shaping element 114. Shaping element 114 alone is not capable of functioning as an antenna; rather shaping element 114 shapes or redistributes the electromagnetic or microwave field emitted by radiating element 112 to produce a clinically improved microwave field. It should be noted that there is no direct electrical conduction between radiating element 112 and shaping element 114. Antenna 104 further comprises one or more antenna dielectrics 116 covering one or more portions of one or both of: radiating element 112 and shaping element 114. Antenna dielectrics 116 shape the microwave field by changing the local dielectric environment in the region wherein antenna dielectrics 116 are located. In FIG. 1A, an antenna dielectric 116 covers the proximal portion of radiating element 112. Any of the antenna dielectrics 116 disclosed herein may be used to shape the microwave field and to optimize the performance of antenna 104. Any of the antenna dielectrics 116 disclosed herein may be replaced by one or more conducting polymers.

Figure 2A:
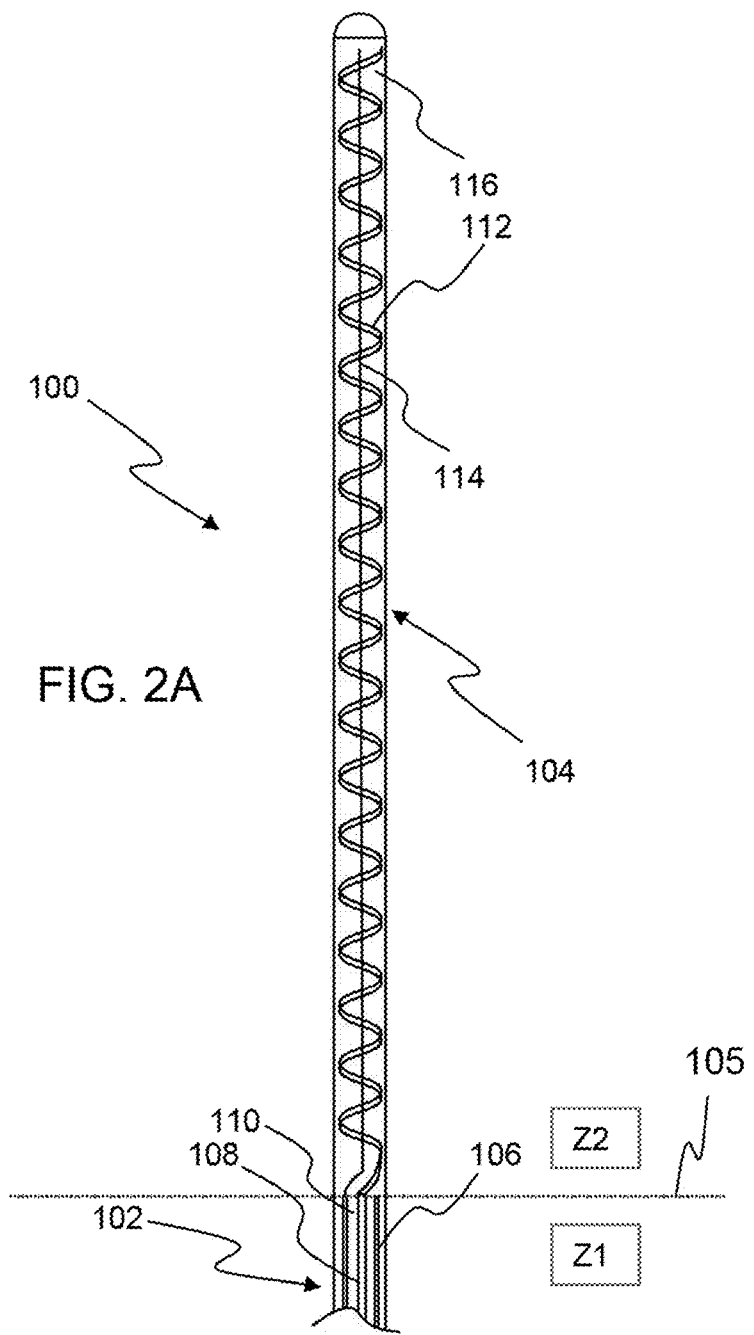
FIG. 2A shows a side view of an embodiment of a linear microwave antenna of the present invention comprising a radiating element and a microwave field shaping element.

A microwave field couples to the nearest conductive path. In prior art monopole antennas such as shown in FIG. 2H, the nearest conductive path is provided by the shielding element of the transmission line (e.g. the outer conductor 106 of the feeding coaxial cable 102). This causes a strong concentration of the microwave field in the junction between antenna 104 and transmission line 102. However, in several embodiments of antenna 104 disclosed herein, the nearest conductive path is provided by shaping element 114. Thus the microwave field couples to shaping element 114 instead of coupling to the shielding element of the transmission line (e.g. the outer conductor 106 of the feeding coaxial cable 102). Therefore, minimal microwave field is coupled proximally to the shielding element of the transmission line. This in turn creates a unique, shaped or redistributed microwave field that does not significantly extend proximally to antenna 104 as shown in FIGS. 2D, 3B, 3F and 4B. Further, the combination of radiating element 112 and shaping element 114 improves the power deposition of antenna 104.

Antennas disclosed herein may comprise one or more shaping elements 114 made of a variety of conducting materials e.g. metals, conductive polymers, materials with embedded conductive particles, etc. Such shaping elements 114 may comprise one or more dielectrics layers to insulate the shaping element 114 from surrounding tissue. Examples of such shaping elements 114 include, but are not limited to: straight or curved segments of metallic elements, elements with a circular or oval shape, elements with a polygonal shape (e.g. triangular, square, rectangular, pentagonal, etc.), multiple elements joined together by one or more electrically conducting joint(s), multiple elements joined together by a non-electrically conducting joint(s), elements with multiple curves, symmetrically arranged segments of elements, non-symmetrically arranged segments of elements, etc. A shaping element 114 may be electrically connected to one or more regions of the shielding element of the transmission line.

In the embodiment shown in FIG. 1A, the width of antenna 104 is substantially greater that the width of the coaxial cable 102. In one embodiment, radiating element 112 is a continuation of the inner conductor 108 of a coaxial cable 102. In a one embodiment, shaping element 114 is made of an electrically conductive material e.g. a metal and is electrically connected to a region of outer conductor 106 of coaxial cable 102. In an alternate embodiment, antenna 104 comprises one or more conductive shaping elements 114 that are electrically isolated from outer conductor 106. In this embodiment, one or more shaping elements 114 function as passive radiators or parasitic elements of antenna 104. In one embodiment, shaping element 114 is designed to act as a microwave shielding element and/or a microwave reflecting element.

Embodiments of antenna 104 may be designed wherein radiating element 112 has no sharp corners. Sharp corners in radiating element 112 may cause the field to concentrate in the vicinity of the sharp corners. Thus embodiments of the present invention may be designed that have minimal or no sharp corners to avoid undesirable regions of concentrated microwave field.

Figure 4A:
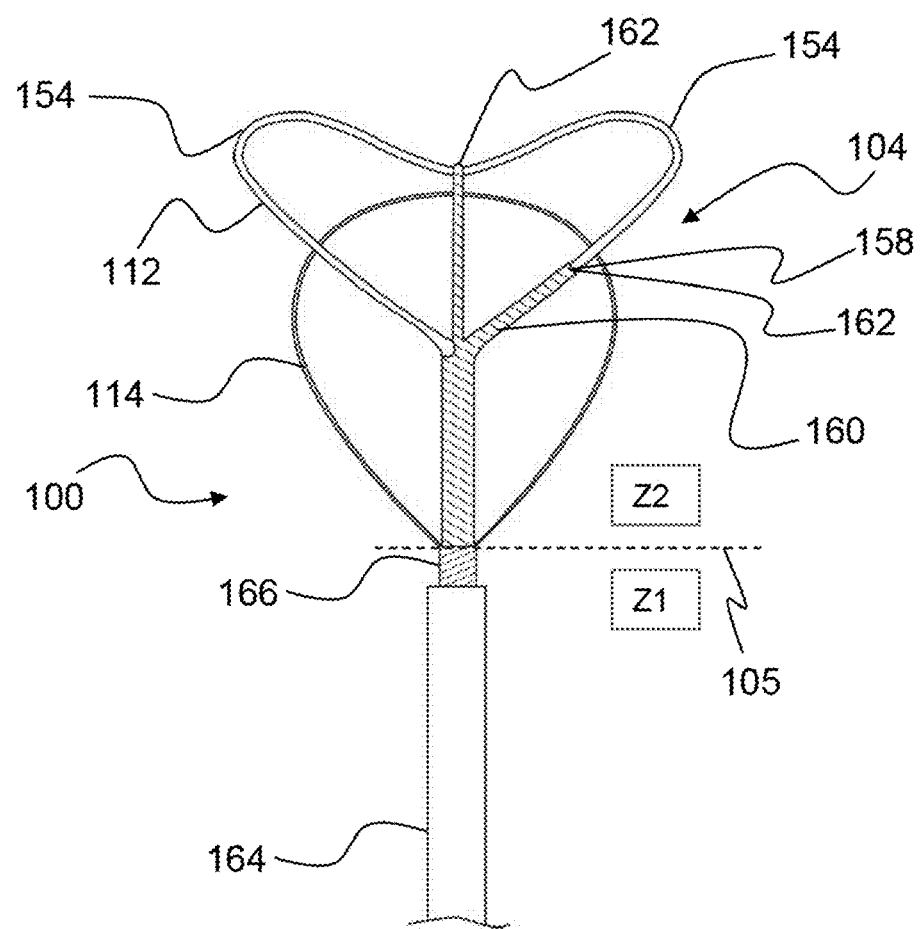
FIG. 4A shows a view of a planar antenna of a microwave ablation device designed for endometrial ablation.

Antenna 104 may be designed to have a shape that substantially approximates the shape of the target tissue to be ablated. In one embodiment, antenna 104 has a roughly triangular shape that is especially suited for endometrial ablation as shown in FIG. 4A. In another embodiment, antenna 104 has a roughly linear shape as shown in FIG. 2A that is especially suited for the ablation of a linear region of tissue e.g. for the creation of a linear lesion in the left atrium.

Further, antenna 104 may be designed to be sufficiently flexible such that during and after introduction and deployment of antenna 104 in the anatomy, the anatomy experiences only slight forces from antenna 104. This may be achieved by designing an antenna 104 comprising one or more flexible radiating elements 112, one or more flexible shaping elements 114 and one or more flexible antenna dielectric materials 116. Sufficiently flexible antennas may reduce damage to healthy tissue as well as potentially reduce the pain experienced by the patient during the introduction and deployment. Antenna 104 may be introduced in a collapsed configuration through a small lumen. The collapsed configuration lowers the overall profile of antenna 104. In the collapsed configuration, radiating element 112 and shaping element 114 may be closer to each other than in the non-collapsed configuration. This enables the introduction of antenna 104 through narrow catheters, shafts, introducers and other introducing devices. Further, this enables the introduction of antenna 104 through small natural or artificially created openings in the body. Further, antenna 104 may be designed to have an atraumatic distal end in which the distal region of antenna 104 is wider and/or sufficiently flexible to reduce the risk of perforation of tissue. The flexible nature of antenna 104 enables antenna 104 to take the natural shape of an introduction passage during introduction instead of distorting the passage. For example, when antenna 104 is introduced via the vasculature into a heart chamber via a femoral vein access, flexible antenna 104 may be easily introduced through the introduction passage comprising the femoral vein access site, femoral vein and the inferior vena cava.

In one embodiment, the length of radiating element 112 measured along the radiating element 112 from the distal end of coaxial cable 102 or other transmission line until the distal end of radiating element 112 is an odd multiple of one quarter of the effective wavelength at one of: 433 MHz ISM band, 915 MHz ISM band, 2.45 GHz ISM band and 5.8 GHz ISM band. For example, the length of radiating element 112 may be three quarters of the effective wavelength at the 915 MHz ISM band. The effective wavelength is dependent on the medium surrounding the antenna and the design of a dielectric covering 116 on the radiating element 112. The design of the dielectric covering includes features such as the type of dielectric(s) and thickness of the dielectric layer(s). The exact length of the radiating element 112 may be designed to get good impedance matching.

In any of the embodiments herein, the proximal portion of radiating element 112 may be a continuation of the inner conductor 108 of coaxial cable 102. The proximal portion of radiating element 112 in any of the embodiments herein may be designed to be stiffer and have a greater mechanical strength than the distal portion of radiating element 112. In one such embodiment, radiating element 112 is a continuation of inner conductor 108 of coaxial cable 102 and dielectric material 110 of coaxial cable 102 is retained on the proximal portion of radiating element 112. In another embodiment, the proximal portion of radiating element 112 is made stiffer by coating the proximal portion of radiating element 112 by a layer of dielectric.

In any of the embodiments herein, one or more outer surfaces of radiating element 112 may be covered with one or more layers of antenna dielectrics 116. The thickness and type of antenna dielectrics 116 along the length of radiating element 112 may be designed to modify and optimize the microwave properties of the antenna 104. For example, one or more antenna dielectrics 116 covering radiating element 112 may be used to shape the microwave field and to optimize the performance of antenna 104. The one or more antenna dielectrics 116 covering radiating element 112 may be used to shape the microwave field by changing the local dielectric environment in the region adjacent to radiating element 112. In any of the embodiments herein, every portion of radiating element 112 may be covered with some antenna dielectric 116 such that no metallic surface of radiating element 112 is exposed to tissue. Thus, radiating element 112 may be electrically insulated from tissue. Thus, in such embodiments, radiating element 112 is able to transmit a microwave field into tissue, but unable to conduct electricity to tissue. Thus, in such embodiments, there is no electrical conduction and no conductive path between radiating element 112 and shaping element 114. Further, in such embodiments, there is no electrical conduction and no conductive path between radiating element 112 and the surrounding tissue. Examples of dielectric materials that can be used to design one or more embodiments disclosed herein include, but are not limited to EPTFE, PTFE, FEP and other fluoropolymers, Silicone, Air, PEEK, polyimides, cyanoacrylates, epoxies, natural or artificial rubbers and combinations thereof. In one embodiment, the dielectric on a proximal portion of radiating element 112 is a continuation of the dielectric 110 of coaxial cable 102. The thickness of a dielectric on radiating element 112 may vary along the length of radiating element 112. Further, the cross section of a dielectric on radiating element 112 may not be radially symmetric. The various configurations of the dielectric may be designed to achieve a desired ablation profile as well as achieve a desired impedance matching or power efficiency. In one embodiment, entire radiating element 112 is covered with a silicone dielectric. The layer of silicone used to coat a distal portion of radiating element 112 may be thinner than the layer of silicone used to coat a proximal portion of radiating element 112. The thinner silicone dielectric may be used to compensate for the lower field strength that normally exists at the distal portion of a microwave antenna. Thus, the microwave field is made more uniform along the length of radiating element 112. In one device embodiment with a silicone dielectric around radiating element 112, radiating element 112 is made of a metallic material and the circumference of the metallic material of a distal region of radiating element 112 is more than the circumference of the metallic material of a proximal portion of radiating element 112. This causes the silicone dielectric to stretch more at the distal portion than at the proximal portion of radiating element 112. This in turn generates a thinner layer of dielectric at the distal portion of radiating element 112 than at the proximal portion of radiating element 112. In another embodiment, entire radiating element 112 is made from a single length of metallic wire of a uniform cross section. In this embodiment, a tubular piece of silicone dielectric of varying thickness may be used to cover radiating element 112. The tubular silicone dielectric is used to cover radiating element 112 such that the layer of silicone dielectric is thinner around a distal portion and thicker around a proximal portion of radiating element 112.

In any of the embodiments herein, the shape of radiating element 112 may be that same or different from the shape of shaping element 114. Further in any of the embodiments herein, both radiating element 112 and shaping element 114 may be non-linear. Further, in any of the embodiments herein, radiating element 112 and shaping element 114 may be non-parallel to each other.

In FIG. 1A, since radiating element 112 is in electrical contact with inner conductor 108, there is a first electrically conductive path extending from inner conductor 108 till the distal end of radiating element 112. In the embodiments wherein shaping element 114 is made of a conductive material and is electrically connected to outer conductor 106 of coaxial cable 102 or other transmission line, there is a second electrically conductive path extending from outer conductor 106 till the distal end of shaping element 114. In such embodiments, even though there are two conductive paths that extend from first zone Z1 to the second zone Z2, the designs, materials and the microwave properties of the two conductive paths may be significantly different in first zone Z1 and second zone Z2. For example, the region of the first conductive path in first zone Z1 is surrounded by the dielectric 110 of coaxial cable 102 whereas the region of the first conductive path in second zone Z2 may be surrounded by one or more dielectric materials or by an anatomical region such as the target tissue. Further, in FIGS. 1A and 1B, the microwave field in first zone Z1 is substantially confined between inner conductor 108 and outer conductor 106 of coaxial cable 102. However, in second zone Z2, the microwave field is non-confined between radiating element 112 and shaping element 114. Further, in first zone Z1, outer conductor 106 of coaxial cable 102 is located symmetrically around inner conductor 108 and at a substantially constant distance from inner conductor 108. However, in second zone Z2, radiating element 112 and shaping element 114 are not located symmetrically relative to each other and the distance between radiating element 112 and shaping element 114 may or may not be constant throughout second zone Z2. Further, outer conductor 106 of coaxial cable 102 is oriented parallel to inner conductor 108 in first zone Z1. But in second zone Z2, radiating element 112 and shaping element 114 may or may not be parallel to each other. However, radiating element 112 and shaping element 114 may both have planar shapes. In one such embodiment, a plane containing radiating element 112 is substantially parallel to a plane containing shaping element 114. In first zone Z1, outer conductor 106 of coaxial cable 102 always acts as a shield for the microwave field in first zone Z1 whereas in second zone Z2, shaping element 114 may or may not act as a shield for the microwave field in second zone Z2. In first zone Z1, the distance between outer conductor 106 and inner conductor 108 may be substantially less than a distance between radiating element 112 and shaping element 114 in second zone Z2.

Although, shaping element 114 in FIG. 1A is shown to be directly electrically connected directly to the shielding element of coaxial cable 102 or other transmission line, shaping element 114 in any of the embodiments disclosed herein may be indirectly connected to the shielding element of the transmission line. In one such embodiment, shaping element 114 is electrically connected indirectly via one or more additional elements (e.g. lengths of metallic wires, solders, conductive fluids, etc.) to the shielding element of the transmission line.

In an alternate embodiment, a microwave field shaping element may be connected to a region of the transmission line proximal to the distal end of the transmission line instead of being connected to the distal end of the transmission line as shown in FIG. 1A. For example, a metallic shaping element 114 may be electrically connected to a region of outer conductor 106 of coaxial cable 102.

Figure 1B:
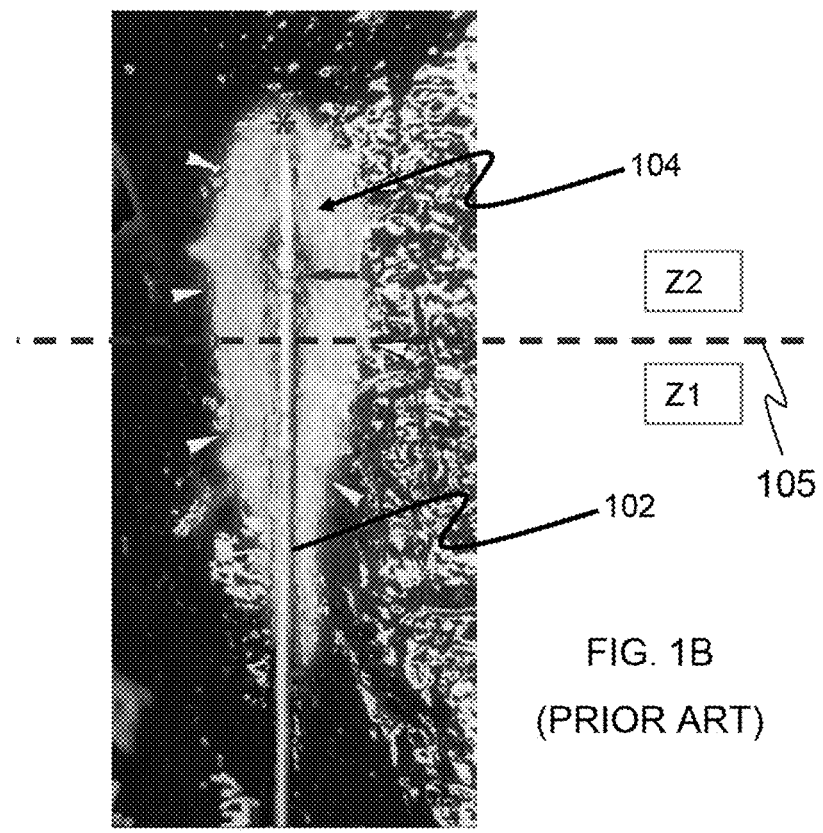
FIG. 1B shows a photograph of the cut surface of swine liver that was ablated using a monopole microwave antenna.
Figure 1C:
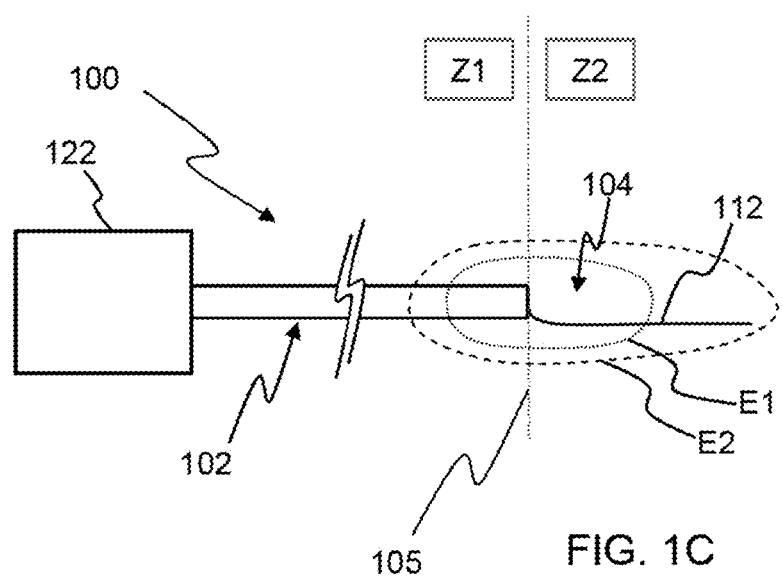
FIG. 1C shows a schematic view of the microwave field emitted by a microwave device comprising an antenna without a shaping element.
Figure 1D:
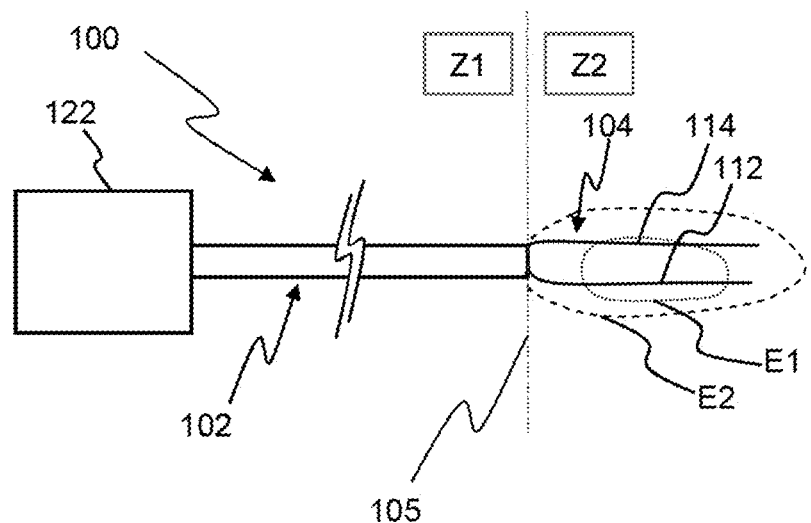
FIG. 1D shows a schematic view of the microwave field emitted by a microwave device comprising an antenna with a shaping element.

FIGS. 1C and 1D are shown to illustrate the general microwave engineering principles used in the design of one or more antennas 104 disclosed herein such as antennas 104 in FIG. 2A, FIG. 3A, FIG. 3F and FIG. 4A. More particularly, FIGS. 1C and 1D shows the microwave effect of adding a shaping member of the present invention to a microwave antenna. FIG. 1C shows a schematic view of the microwave field emitted by a microwave device comprising an antenna without a shaping element. FIG. 1D shows a schematic view of the microwave field emitted by a microwave device comprising an antenna with a shaping element. In FIGS. 1C and 1D, a microwave source 122 (e.g. a microwave generator) transmits microwave energy to an antenna 104 by a transmission line 102 (e.g. a coaxial cable). E1 shows the boundary of a first high intensity level of the microwave field. E2 shows the boundary of a second low intensity level of the microwave field. In FIG. 1C, a microwave field is emitted by antenna 104 comprising radiating element 112. The emitted microwave field couples to the nearest conductive path. In this embodiment, since there is no shaping element 114, the nearest conductive path is provided by the distal region of the transmission line (e.g. outer conductor 106 of a feeding coaxial cable 102). Thus, the microwave field couples to the distal region of the transmission line (backward coupling). This in turn induces an induced current on the surface of the shielding element of the transmission line. This induced current in turn generates a second microwave field around the distal region of the transmission line. Thus, the microwave field is shifted proximally. There is a strong concentration of the microwave field in the junction between antenna 104 and transmission line 102 as shown in FIG. 1C. The highest intensity of the microwave field is located at the junction region between antenna 104 and transmission line 102. Thus, a significant portion of the microwave field is located in zone Z1. This portion of the microwave field can generate heat that affects healthy tissue and increases the morbidity of the medical procedure. Further, a significant portion of the microwave field is located around the distal region of transmission line 102. This field can cause heating of the distal region of transmission line 102. A hot distal region of transmission line 102 can damage surrounding tissue and increase the morbidity of the medical procedure. Further, since only a fraction of the emitted microwave field is deposited in zone Z2, the power deposition of antenna 102 is lowered. A significant portion of the field is wasted in zone Z1.

In FIG. 1D, a microwave field is emitted by antenna 104 comprising radiating element 112 and shaping element 114. Shaping element 114 extends along at least a portion of radiating element 112 and is in the vicinity of radiating element 112 as shown. The proximal portion of shaping element 114 is electrically connected to the shielding element on a distal region (e.g. on or near the distal end) of transmission line 102. The microwave field emitted by radiating element 112 couples to the nearest conductive path. In this embodiment, the nearest conductive path is provided by the conductive shaping element 114 instead of the shielding element of the distal region of the transmission line. Thus, the microwave field emitted by radiating element 112 couples to the conductive shaping element 114 instead of coupling to the shielding element of the distal region of the transmission line. This induces a leakage current on shaping element 114. The leakage current in turn creates a second microwave field. The first microwave field and the second microwave field together combine to produce a unique, shaped microwave field of antenna 104 that is significantly more advantageous that the unshaped microwave field generated by an antenna 104 comprising only radiating element 112 in FIG. 1C. Thus the original microwave field is redistributed by the design of shaping element 114. This causes a strong concentration of the microwave field around antenna 104 as shown in FIG. 1D. The presence of shaping element 114 has prevented the microwave field from coupling to the distal region of the transmission line 102. That is the presence of shaping element 114 has prevented the backward coupling of microwave field with the distal region of the transmission line 102. The highest intensity of the microwave field is located around antenna 104. Thus, virtually all the microwave field is located in zone Z2 and virtually no microwave field is located proximal to antenna 104. This in turn substantially reduces or eliminates the heating up of the distal region of the transmission line 102. Thus, the embodiment in FIG. 1D has a significantly reduced risk of damaging healthy tissue which in turn increases the safety of the medical procedure. Further, virtually none of the microwave field is located around the distal region of transmission line 102. Thus, the risk of heating up the distal region of transmission line 102 is minimized or eliminated. Further, since a vast majority of the emitted microwave field is deposited in zone Z2, the power deposition of antenna 102 is improved. Virtually no portion of the field is wasted in zone Z1.

Further, as shown in FIGS. 1C and 1D, the use of shaping element 114 has changed the shape of the microwave field emitted by antenna 104. Such use of one or more shaping elements allows the purposeful designing of antennas that can be tailored to a specific clinical application. Thus a microwave antenna designer is no longer restricted to using only the existing linear antenna geometries. Rather, he has the freedom to use the most suitable geometry (e.g. linear, non-linear planar, 3-dimensional, etc.) that is best suited for the specific clinical application. Thus various embodiments of antenna 104 may be designed to generate a variety of shapes of SAR and/or the ablation profile. For example, antennas 104 may be designed to generate substantially square, triangular, pentagonal, rectangular, round or part round (e.g. half round, quarter round, etc.), spindle-shaped or oval SARs or ablation patterns. One benefit available to a variation of a device designed according to the teachings herein is the ability to design microwave antennas that can generate a desired microwave field profile while having improved power deposition and a high impedance matching over a wider bandwidth.

The following figures illustrate some specific examples of microwave antennas designed using the principles disclosed herein. For illustration purposes, a linear, planar and a 3-dimensional antenna are shown to illustrate that the microwave design principles disclosed herein may be applied to design a wide range of antennas. FIG. 2A shows a side view of an embodiment of a linear microwave antenna of the present invention comprising a radiating element and a microwave field shaping element. In the embodiment shown in FIG. 2A, the novel microwave field shaping technique of the present invention is used to improve the performance of a helical antenna. The resultant antenna can be used to create a uniform lesion along the length of the antenna without adversely affecting tissues surrounding the transmission line. In FIG. 2A, microwave ablation device 100 comprises a transmission line such as a coaxial cable 102. An antenna 104 is connected to the distal end of coaxial cable 102. In the embodiment shown in FIG. 2A, the width of antenna 104 is substantially the same as the width of the coaxial cable 102. FIG. 2A shows microwave ablation device 100 divided into a first zone Z1 and a second zone Z2 by an imaginary transition line 105. First zone Z1 is proximal to second zone Z2. Transition line 105 in FIG. 2A is defined by the distal end of coaxial cable 102 and is substantially perpendicular to the axis of coaxial cable 102 at the distal end of coaxial cable 102. In the embodiment shown in FIG. 2A, the distal region of coaxial cable 102 lies entirely within first zone Z1 and antenna 104 lies entirely within second zone Z2. In one embodiment, a single microwave signal is fed to antenna 104 through coaxial cable 102. Antenna 104 generates a microwave field. The near field of the microwave field generated by antenna 104 may be used for achieving the desired clinical outcome such as ablating tissue. In FIG. 2A, antenna 104 comprises a radiating element 112 and a shaping element 114. In one embodiment, radiating element 112 is a continuation of the inner conductor 108 of coaxial cable 102. Shaping element 114 shapes the microwave field emitted by radiating element 112. In FIG. 2A, shaping member 114 is located distal to the distal end of coaxial cable 102 (in zone Z2). In one embodiment, shaping element 114 is made of an electrically conductive material e.g. a metal or a conductive polymer and is electrically connected to a region of outer conductor 106 of coaxial cable 102. In an alternate embodiment, a conductive shaping element 114 is electrically isolated from outer conductor 106. In this embodiment, shaping element 114 functions as a passive radiator or parasitic element of antenna 104. Shaping element 114 in this electrically isolated embodiment absorbs microwaves radiated from radiating element 112 and re-radiates microwaves. Referring back to FIG. 2A, it should be noted that there is no direct electrical conduction between radiating element 112 and shaping element 114. When microwave energy is delivered through coaxial cable 102 to antenna 104 in FIG. 2A, a first microwave field is emitted by radiating element 112. This first microwave field is a normal mode microwave field of a small diameter (antenna diameter D is much less than microwave wavelength) helical antenna. The first microwave field interacts with shaping element 114. This interaction induces a leakage current on shaping element 114. The leakage current in turn creates a second microwave field. The second microwave field is an elongated, axial mode microwave field due to the elongate shape of shaping element 114. The first microwave field and the second microwave field together combine to produce a unique shaped microwave field of antenna 104 that is clinically more useful that the unshaped microwave field generated by an antenna 104 comprising only radiating element 112. Thus the original microwave field is redistributed by the design of shaping element 114.

Further, the specific design of shaping element 114 may be used to improve the power deposition of an antenna 104 comprising radiating element 112. Shaping element 114 may be made of one or more non-insulated or insulated elements. Examples of such elements include, but are not limited to: straight or curved segments of metallic elements, elements with a circular or oval shape, elements with a polygonal shape (e.g. triangular, square, rectangular; pentagonal, etc.), multiple elements joined together by an electrically conducting joint(s), multiple elements joined together by a non-electrically conducting joint(s), elements with multiple curves, symmetrically arranged segments of elements, non-symmetrically arranged segments of elements, elements comprising outer coatings or layers of non-conducting materials, etc.

The embodiment of antenna 104 shown in FIG. 2A has a linear shape that is especially suited for the ablation of a linear region of tissue e.g. for the creation of a linear lesion in the left atrium.

In FIG. 2A, the surface of radiating element 112 is enclosed within one or more layers of dielectric materials.

The thickness and type of dielectric material along the length of radiating element 112 is engineered to optimize the microwave field shape. Thus one or more dielectric materials covering radiating element 112 may also be used as non-conducting shaping elements to shape the microwave field. The one or more dielectric materials covering radiating element 112 shape the microwave field by changing the local dielectric environment in the region adjacent to radiating element 112. In this embodiment, every portion of radiating element 112 is covered with some dielectric material such that no metallic surface of radiating element 112 is exposed to tissue. Thus, in this embodiment, radiating element 112 is electrically insulated from tissue. Thus, in this embodiment, radiating element 112 is able to transmit a microwave field into tissue, but unable to conduct electricity to tissue. Thus, in this embodiment, there is no electrical conduction and no conductive path between radiating element 112 and shaping element 114. Further, in this embodiment, there is no electrical conduction and no conductive path between radiating element 112 and the surrounding tissue. In one embodiment, the dielectric on a proximal portion of radiating element 112 is a continuation of the dielectric 110 of coaxial cable 102. The thickness of a dielectric on radiating element 112 may vary along the length of radiating element 112. Further, the cross section of a dielectric on radiating element 112 may not be radially symmetric.

In the embodiment of FIG. 2A, radiating element 112 is non-linear and is made of a helically arranged length of a metallic conductor. The helix may be symmetric with a constant pitch and a constant diameter along the length of the helix. In one embodiment, the straightened length of the conductor used for constructing radiating element 112 is about three quarters of the effective wavelength at 915 MHz. In alternate embodiments, this length may be an odd multiple of one quarter of the effective wavelength at one of: 433 MHz ISM band, 915 MHz ISM band, 2.45 GHz ISM band and 5.8 GHz ISM band. Although in FIG. 2A, radiating element 112 has about 19 turns, embodiments of ablation devices 100 may be constructed wherein radiating element 112 has about 1 to 30 turns. The pitch of a helical radiating element 112 may range between 0.3 mm and 20 mm. Radiating element 112 may be made from a metallic element or alloy selected from the group comprising Nitinol, stainless steel or copper. Radiating element 112 may comprise a plating of a conducting metal such as Ag or Au on the outer surface of radiating element 112. The metallic conductor used for constructing radiating element 112 may have a round, oval, rectangular or square cross section. In one embodiment, the metallic conductor used for constructing radiating element 112 has a round cross section with a diameter of 0.5 mm+/−0.4 mm. In another embodiment, the metallic conductor used for constructing radiating element 112 has a rectangular cross section with cross sectional dimensions of 10 mm+/−9.5 mm by 0.5 mm+/−0.4 mm. In another embodiment of a radiating element with a rectangular cross section, the cross sectional dimensions are 1 mm+/−0.3 mm by 0.1 mm+/−0.05 mm. In an alternate embodiment, radiating element 112 is made of a length of a metallic conductor that is arranged in a substantially two dimensional configuration. For example, the length of a metallic conductor may be arranged in a substantially wavy or zigzag or serpentine configuration. In the embodiment in FIG. 2A, radiating element 112 is arranged symmetrically around shaping element 114 and partially or fully encloses shaping element 114. Shaping element 114 may be made of a linear or helical length of a metallic conductor. The outer diameter of shaping element 114 may be uniform or may be non-uniform along the length of antenna 104. In the embodiment shown in FIG. 2A, shaping element 114 is made of a substantially linear length of a metallic conductor. Shaping element 114 may be made from a metallic element or alloy selected from the group comprising Nitinol, stainless steel or copper. Shaping element 114 may comprise a plating of a conducting metal such as Ag or Au on the outer surface of shaping element 114. The metallic conductor used for constructing shaping element 114 may have a round, oval, rectangular or square cross section. In one embodiment, the metallic conductor used for constructing shaping element 114 has a round cross section with a diameter of 0.5 mm+/−0.3 mm. In another embodiment, the metallic conductor used for constructing shaping element 114 has a rectangular cross section with dimensions of 0.5 mm+/−0.3 mm by 0.5 mm+/−0.3 mm. Antenna 104 further comprises one or more antenna dielectrics 116 between radiating element 112 and shaping element 114. In one embodiment, antenna dielectric 116 is sufficiently flexible to create a flexible antenna 104. The flexibility of antenna 104 allows antenna 104 to bend from a substantially straight, linear configuration to a substantially non-linear configuration and vice-versa during clinical use. The flexibility of antenna 104 also allows antenna 104 to bend relative to the distal end of the transmission line during clinical use. This in turn allows a user to introduce antenna 104 to the target location through tortuous or non-linear introduction paths such as blood vessels. In one embodiment, antenna dielectric 116 is sufficiently stiff to create a sufficiently stiff antenna 104. The stiffness of antenna 104 prevents antenna 104 from bending during clinical use. This in turn enables the user to use antenna 104 to puncture or penetrate through tissue such as tumor tissue. Such embodiments of antenna 104 may be used for ablating solid volumes of tissues such as solid tumors. Examples of dielectrics that can be used between radiating element 112 and shaping element 114 include, but are not limited to EPTFE, PTFE, FEP and other fluoropolymers, Silicone, Air, PEEK, polyimides, natural or artificial rubbers and combinations thereof. Additionally the entire antenna 104 may be covered or encapsulated in a dielectric. Examples of dielectrics that can be used to cover or encapsulate antenna 104 include, but are not limited to EPTFE, PTFE, FEP and other fluoropolymers, Silicone, PEEK, polyimides, natural or artificial rubbers and combinations thereof. Antenna dielectric 116 may comprise one or more layers of such dielectrics. The dielectric used to cover or encapsulate antenna 104 may be porous or non-porous. In FIG. 2A, the length of antenna 104 is between 10 mm and 80 mm. In FIG. 2A, the width of antenna 104 is between 1 mm and 40 mm. In one particular embodiment, antenna 104 has a length of 45 mm+/−7 mm and a width of 2 mm+/−0.5 mm. Radiating element 112 is electrically connected to inner conductor 108 of coaxial cable 102. This may be done for example, by soldering or resistance welding radiating element 112 to inner conductor 108. Radiating element 112 may be a continuation of inner conductor 108 of coaxial cable 102. Shaping element 114 is electrically connected to outer conductor 106 of coaxial cable 102. This may be done for example, by soldering or resistance welding shaping element 114 to outer conductor 106. Antenna 104 may be floppy, flexible or substantially rigid. Antenna 104 may be malleable or have shape memory or elastic or super-elastic properties. The distal end of antenna 104 may be atraumatic. Antenna 104 may be designed such that the length of antenna 104 is adjustable. For example, length of antenna 104 may be increased or reduced to increase or reduce the length of an ablation zone. In this embodiment, shaping element 114 may have a helical or substantially wavy or zigzag or serpentine configuration. The length of antenna 104 may be increased or reduced intra-operatively or pre-operatively. In one embodiment, the length and/or the diameter of the ablation zone is changed by one or more of: changing the length of radiating element 112, changing the length of shaping element 114, changing the shape of radiating element 112, changing the shape of shaping element 114 and changing the relative positions of radiating element 112 and shaping element 114. In one embodiment, one or both of radiating element 112 and shaping element 114 are a part of a flexible circuit and are manufactured using commonly known techniques for manufacturing flexible circuits.

In FIG. 2A, the shape of radiating element 112 is different from the shape of shaping element 114. Further in the embodiment in FIG. 2A, radiating element 112 is non-linear. Further in the embodiment in FIG. 2A, shaping element 114 is substantially linear. However radiating element 112 and shaping element 114 are generally oriented such that their axes are parallel to each other. Alternate embodiments of antenna 104 may be designed wherein radiating element 112 is substantially linear. Alternate embodiments of antenna 104 may be designed wherein shaping element 114 is substantially non-linear. Alternate embodiments of antenna 104 may be designed wherein radiating element 112 and shaping element 114 are generally oriented such that their axes are not parallel.

Although in the embodiment in FIG. 2A shaping element 114 is connected to the distal end of coaxial cable 102, other embodiments of antenna 104 may be designed wherein shaping element 114 is connected to coaxial cable 102 at a region other than the distal end of coaxial cable 102. For example, in one alternate embodiment, shaping element 114 is metallic and is electrically connected to a region of outer conductor 106 of coaxial cable 102 proximal to the distal end of the coaxial cable 102.

In FIG. 2A, since radiating element 112 is in electrical contact with inner conductor 108, there is a first electrically conductive path extending from inner conductor 108 till the distal end of radiating element 112. In the embodiments wherein shaping element 114 is made of a conductive material and is electrically connected to outer conductor 106 of coaxial cable 102, there is a second electrically conductive path extending from outer conductor 106 till the distal end of shaping element 114. In such embodiments, even though there are two conductive paths that extend from first zone Z1 to the second zone Z2, the designs, materials and the microwave properties of the two conductive paths may be significantly different in first zone Z1 and second zone Z2 as described before. In first zone Z1, outer conductor 106 of coaxial cable 102 is located symmetrically around inner conductor 108 and at a constant distance from inner conductor 108. However, in second zone Z2, radiating element 112 is located symmetrically around shaping element 114 and at a constant distance from shaping element 114. In first zone Z1, outer conductor 106 of coaxial cable 102 always acts as a shield for the microwave field in first zone Z1 whereas in second zone Z2, shaping element 114 may or may not act as a shield for the microwave field in second zone Z2.

FIG. 2B shows a section through an embodiment of coaxial cable 102 usable for ablation device 100 of FIG. 2A and for other ablation devices 100 disclosed herein. In one embodiment, coaxial cable 102 used herein is flexible and comprises an inner conductor 108 made of Nitinol with a Ni content of 56%+/−5%. The outer diameter of inner conductor 108 is 0.0172"+/−0.004". Inner conductor 108 has a cladding or plating 120 of a highly conductive metal such as Ag or Au. In one embodiment, inner conductor 108 comprises a silver cladding 120 of thickness 0.000250"+/−0.000050". Cladding 120 in turn is surrounded by dielectric material 110. In embodiment, dielectric material 110 is made of expanded PTFE with an outer diameter of 0.046"+/−0.005". The dielectric material 110 in turn is surrounded by the outer conductor 106. Outer conductor 106 acts as a shielding element to the microwave signals transmitted by inner conductor 108. Further, outer conductor 106 shields the microwave signals transmitted by inner conductor 108 from external noise. In one embodiment, outer conductor 106 comprises multiple strands of Ag plated Cu. The multiple strands of outer conductor 106 are arranged such that the outer diameter of outer conductor 106 is 0.057"+/−0.005". Outer conductor 106 in turn is covered by an outer jacket 118. In one embodiment, outer jacket 118 is made of PTFE with an outer diameter of 0.065"+/−0.005". Thus, the outer diameter of coaxial cable 102 is less than about 2 mm. The low profile of flexible coaxial cable 102 has significant clinical advantages since it can be inserted through narrow and/or tortuous anatomical paths or introducing device lumens. In one embodiment, a shaft comprising coaxial cable 102 is stiffened or strengthened by adding one or more stiffening or strengthening elements such as enclosing stiffening devices jackets, braids, or stiffening layers over coaxial cable 102. In one embodiment, antenna 104 is stiffened or strengthened by adding one or more stiffening or strengthening elements such as jackets, braids or layers within or over antenna 104.

FIG. 2C shows a longitudinal section of the embodiment of ablation device 100 of FIG. 2A through the distal end of coaxial cable 102. In FIG. 2C, the identity of coaxial cable 102 ends at the distal end of outer conductor 106. Transition line 105 in FIG. 2C is located at the distal end of outer conductor 106 and is substantially perpendicular to the axis of coaxial cable 102 at the distal end of outer conductor 106. Outer jacket 118 of coaxial cable 102 terminates a small distance proximal to the distal end of outer conductor 106. A length of a conductive element extending distally from the distal end of inner conductor 108 forms radiating element 112. In one embodiment, radiating element 112 is a continuation of inner conductor 108. In another embodiment, radiating element 112 is length of a conductor attached to inner conductor 108. In one embodiment, the proximal end of radiating element 112 is electrically connected to the distal end of inner conductor 108. In one embodiment, the proximal end of radiating element 112 is soldered to inner conductor 108. In another embodiment, the proximal end of radiating element 112 is laser welded to inner conductor 108. The proximal end of radiating element 112 may be electrically connected to inner conductor 108 in various configurations including, but not limited to lap joint and butt joint. The proximal end of shaping element 114 is electrically connected to a region of outer conductor 106. In one embodiment, the proximal end of shaping element 114 is electrically connected to the distal end of outer conductor 106. In one embodiment, the proximal end of shaping element 114 is soldered to outer conductor 106. In another embodiment, the proximal end of shaping element 114 is laser welded to outer conductor 106. The proximal end of shaping element 114 may be electrically connected to outer conductor 106 in various configurations including, but not limited to lap joint and butt joint.

Figure 2D:
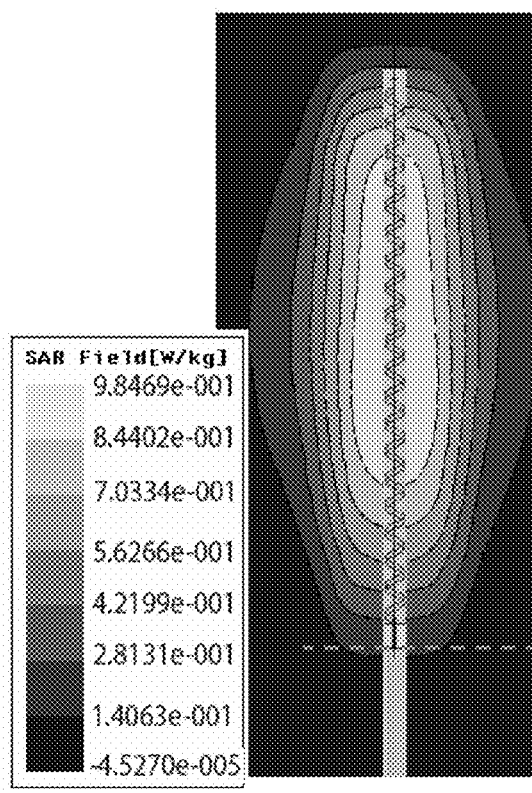
FIGS. 2D and 2E show two side views of a simulated SAR profile generated by the device embodiment of FIG. 2A.
Figure 2E:
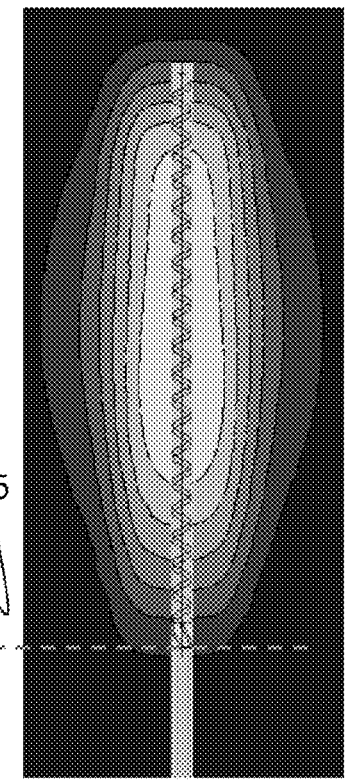

FIGS. 2D and 2E show two side views of a simulated SAR profile generated by the device embodiment of FIG.

Figure 2F:
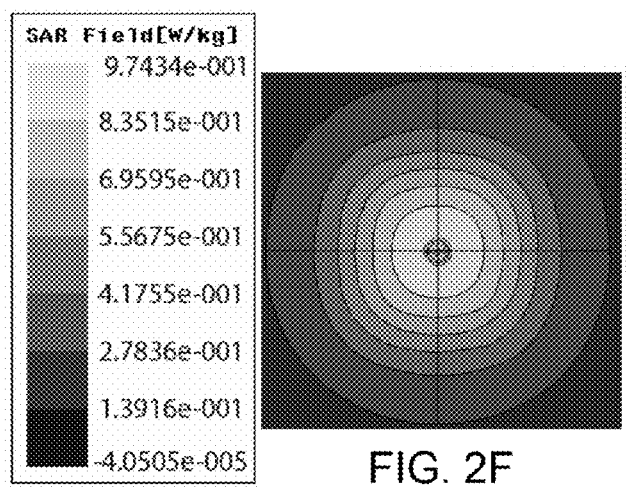
FIG. 2F shows a top view of a simulated SAR profile generated by the device embodiment of FIG. 2A.

2A. FIG. 2F shows a top view of a simulated SAR profile generated by the device embodiment of FIG. 2A. FIG. 2F demonstrates that the SAR profile generated by the device embodiment of FIG. 2A is substantially radially symmetric and circumferentially and volumetrically envelops entire antenna 104. This entire circumferentially and volumetrically enveloping microwave field around antenna 104 can be delivered to the target tissue. FIGS. 2D and 2E demonstrate that the microwave field generated by antenna 104 of FIG. 2A is substantially restricted to second zone Z2. There is an insignificant amount of the microwave field in first zone Z1 containing coaxial cable 102. Thus, there is negligible backward coupling between the microwave field and the distal portion of coaxial cable 102. This in turn reduces the risk of ablating tissue proximal to the distal end of coaxial cable 102. Further, the microwave field is substantially uniform along the length of antenna 104 as compared to a comparable monopole antenna. Thus the lesion formed by the microwave field in FIGS. 2D and 2E will be uniform and substantially localized to the extent of antenna 104. Also, FIGS. 2D and 2E show that the microwave field volumetrically envelops entire antenna 104. Thus, embodiments of linear antenna 104 designed to operate at 915 MHz and other microwave frequencies may be designed that can create uniform, symmetrical, continuous, linear or volumetric lesions with a lesion length greater than 35 mm.

In alternate embodiments, the SAR profile may be designed to be substantially non-uniform along the length of a linear antenna 104. For example, an antenna 104 may be designed to have a SAR profile that is wider and/or stronger at the center of antenna 104 and is less strong at the ends of antenna 104. In order to achieve this, one or more design parameters of antenna 104 in FIG. 2A may be modified. Examples of such modifications include, but are not limited to: adding of one or more additional conductive shaping elements 114; varying the width and/or the cross section shape of shaping element 114 and/or radiating element 112 along the length of antenna 104; varying the pitch of helical radiating element 112 and/or helical shaping element 114 along the length of antenna 104; varying the thickness, type and other design parameters of one or more antenna dielectrics 116, etc.

Antenna 104 in FIG. 2A has several advantages over a comparable monopole antenna. FIGS. 2H and 2I show a side view and the top view respectively of a simulated SAR profile generated by a monopole antenna. The microwave field colors in FIG. 2I are coded according to the same scale shown in FIG. 2H. FIG. 2H shows the presence of a region of concentrated microwave field or a "hot spot" near the distal end of the transmission line (e.g. a coaxial cable) or at the proximal end of the monopole antenna. Thus the microwave field in FIG. 2H is non-uniform as compared to the field in FIG. 2D. About half of the microwave field in FIG. 2H is present in first zone Z1. Thus, there is a significant amount of microwave field present in first zone Z1. Thus, there is a high risk of ablating tissue proximal to the distal end of coaxial cable 102. The presence of a significant amount of microwave field in first zone Z1 is due to undesirable coupling between the microwave field and the outer conductor of the coaxial cable or other transmission line. This undesirable coupling can also cause backward heating of coaxial cable 102 that may lead to collateral damage of healthy tissue as shown in FIG. 1B.

In several of the embodiments herein, shaping element 114 plays a critical role in shaping the microwave field generated by antenna 104. FIG. 2J shows a side view of a simulated SAR profile generated by the device embodiment of FIG. 2A without shaping element 114. The microwave field shown in FIG. 2J is an unshaped field since it is not shaped by shaping element 114. It is seen that antenna 104 in FIG. 2J behaves similar to a monopole antenna of FIG. 2H. FIG. 2J shows the presence of a region of concentrated microwave field or a "hot spot" near the distal end of the coaxial cable 102 or at the proximal end of the antenna 104. Thus the unshaped microwave field in FIG. 2J is non-uniform as compared to the shaped microwave field shaped by shaping element 114 in FIG. 2D. About half of the unshaped microwave field in FIG. 2J is present in first zone Z1. Thus, there is a significant amount of microwave field present in first zone Z1. Thus, there is a high risk of ablating tissue proximal to the distal end of coaxial cable 102. The presence of a significant amount of microwave field in first zone Z1 is due to undesirable coupling between the microwave field and the outer conductor of the coaxial cable 102 or other transmission line. This undesirable coupling can also cause backward heating of coaxial cable 102 that may lead to collateral damage of healthy tissue.

When the SAR profiles in FIGS. 2D and 2J are compared, the effect of shaping element 114 is clear. In the embodiment of FIG. 2D, the nearest conductive path is provided by the conductive shaping element 114 instead of the shielding element of the distal region of the transmission line 102. The presence of shaping element 114 has prevented the microwave field from coupling to the distal region of the transmission line 102. Virtually none of the microwave field is located around the distal region of transmission line 102. Further, since a vast majority of the emitted microwave field is deposited in zone Z2, the power deposition of antenna 102 is improved. Virtually no portion of the field is wasted in zone Z1.

Figure 2G:
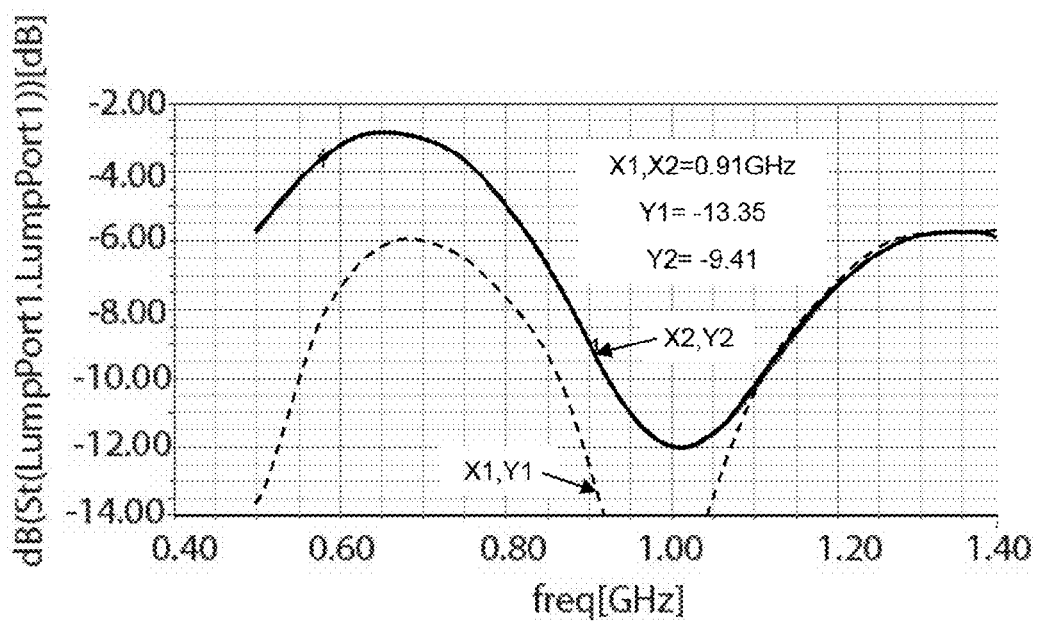
FIG. 2G shows the simulated return loss (solid line) of an ablation device with an antenna of FIG. 2A without a shaping element.
Figure 2H:
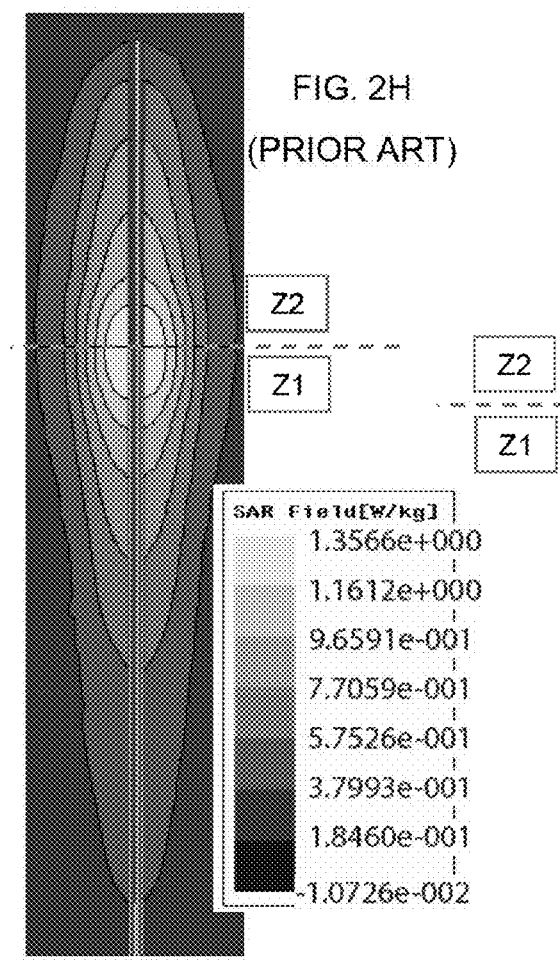
FIGS. 2H and 2I show a side view and the top view respectively of a simulated SAR profile generated by a monopole antenna.
Figure 2J:
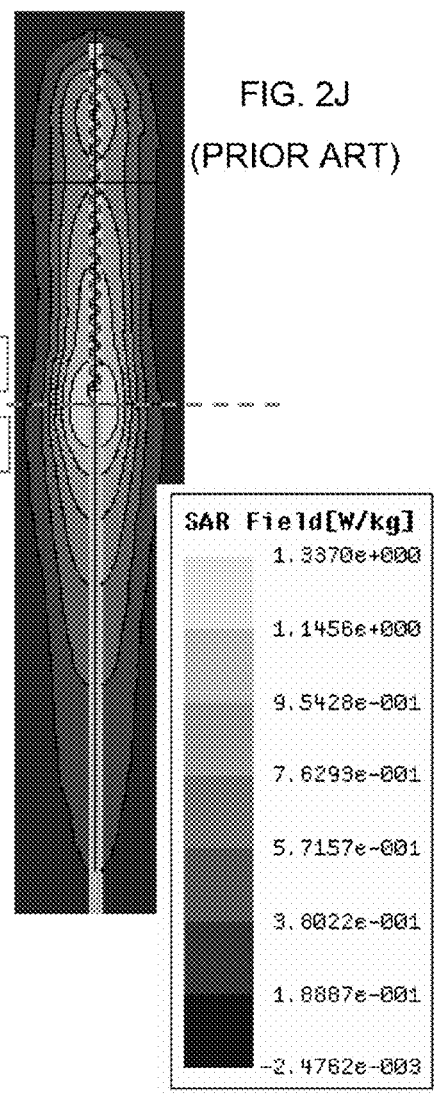
FIG. 2J shows a side view of a simulated SAR profile generated by the device embodiment of FIG. 2A without a shaping element.
Figure 2I:
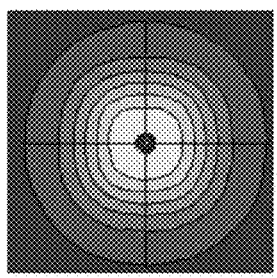

FIG. 2G shows the simulated return loss (solid line) of an ablation device with an antenna of FIG. 2A without shaping element 114. The simulated return loss shows a matching of −9.41 dB at 915 MHz that is inferior than the good matching (about −13.35 dB) at 915 MHz obtained with the antenna of FIG. 2A (dashed line in FIG. 2G). Thus, the design of shaping element 114 in antenna 104 of FIG. 2A improves the matching and reduces the return loss.

Shaping element 114 may be used to provide an additional resonance point in the frequency spectrum. This in turn may be used to increase the frequency range (bandwidth) over which antenna 104 delivers an acceptable performance. For example, the design of shaping element 114 in FIG. 2A improves the frequency range over which important performance parameters are acceptable. In FIG. 2G if the solid and dashed lines are compared, at a cutoff of −10 dB, the acceptable frequency range between 0.8 GHz to 1.2 GHz in the embodiment containing shaping element 114 is about 0.23 GHz (spanning from approximately 0.87 GHz to approximately 1.10 GHz). The acceptable frequency range between 0.8 GHz to 1.2 GHz in the comparable embodiment of FIG. 2J without shaping element 114 is only about 0.19 GHz (spanning from approximately 0.93 GHz to approximately 1.12 GHz). Thus in the first case, a larger frequency range (bandwidth) is available over which antenna 104 delivers an acceptable performance. This in turn allows for a design of antenna 104 wherein minor distortions of antenna 104 during typical clinical use or due to minor manufacturing variations do not significantly affect the performance of antenna 104.

In one particular embodiment of antenna 104 of FIG. 2A, dielectric 116 is transparent and flexible. The linear length of antenna 104 from the distal end of coaxial cable 102 till the distal end of radiating element 112 is about 4.5+/−0.5 cm.

Alternate embodiments of antenna 104 may be designed with a linear length ranging from 2.5-5.5 cm. In the particular embodiment, the outer diameter of antenna 104 is about 2 mm. Alternate embodiments of antenna 104 may be designed with an outer diameter ranging from 1.5-4 mm.

In one method embodiment, antenna 104 of FIG. 2A is inserted inside a chamber of the heart such as the left atrium. Thereafter, microwave power is delivered to the heart tissue by antenna 104 to create a first lesion. Thereafter, antenna 104 is repositioned inside the heart chamber. Thereafter, microwave power is delivered to the heart tissue by antenna 104 to create a second lesion such that the first lesion and second lesion overlap. The lesions may be created e.g. by delivering microwave power at 0.915 GHz at 80 W for 60 s. Antenna 104 may be bent during clinical use without adversely affecting its microwave characteristics. Further details and examples of various method and device embodiments that may be constructed using the microwave antennas and microwave engineering concepts disclosed herein are disclosed in U.S. Provisional Patent Application Ser. No. 61/222,409 Filed: Jul. 1, 2009 and U.S. patent application Ser. No. 12/603,077 Filed: Oct. 21, 2009, the entire disclosures of which are incorporated herein by reference.

In one method embodiment, a radiating element 112 and a shaping element 114 of an antenna 104 are placed on opposite sides of a target tissue to be treated. In one such example, ablation device 100 is introduced in a lumen or a body cavity. Examples of such lumens or body cavities include but are not limited to: natural or artificially created cavities or lumens in portions of the male urinary tract, gall bladder, uterus and other portions of the female reproductive tract, regions of the vasculature, intestine and other portions of the lower alimentary tract, stomach and other portions of the upper alimentary tract, liver and other digestive organs, lungs, skin, mucus membranes, kidneys, reproductive organs, or other organs or soft tissues of the body. Antenna 104 is positioned near the target tissue such that radiating element 112 is located in the lumen while shaping element 114 is located outside the lumen. Shaping element 114 may be located inside the tissue of the wall of lumen or may be passed through a natural or artificially created opening to a location outside the lumen. Shaping element 114 shapes the microwave field emitted by radiating element 112 such that the microwave field is concentrated in the region between radiating element 112 and shaping element 114. This concentrated microwave field in the region between radiating element 112 and shaping element 114 is used to ablate tissue. In an alternate embodiment, shaping element 114 is located in the lumen while radiating element 112 is located outside the lumen.

In one method embodiment, a target tissue is located between an antenna 104 and a microwave shield or reflector. Thereafter, microwave energy is delivered to treat the target tissue.

In any of the embodiments herein, the whole or portions of antenna 104 may be printed on one or more rigid or flexible, planar or non-planar printed circuit boards.

Figure 3A:
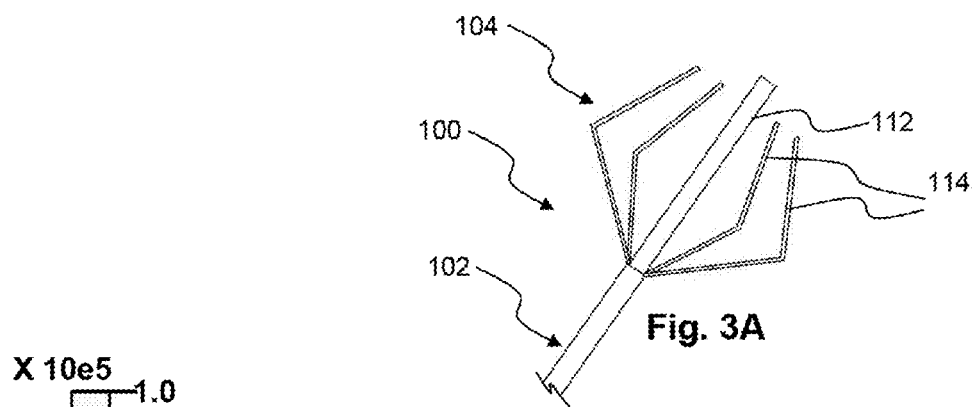
FIG. 3A shows an embodiment of an ablation device with a three dimensional antenna comprising a radiating element and multiple shaping elements adapted to ablate a volume of tissue.

FIG. 3A shows an embodiment of an ablation device with a three dimensional antenna comprising a radiating element and multiple shaping elements adapted to ablate a volume of tissue. In FIG. 3A, ablation device 100 comprises an antenna 104 comprising a substantially linear radiating element 112. Antenna 104 further comprises a plurality of shaping elements 114. In FIG. 3A, the four shaping elements 114 are identical and are arranged symmetrically around radiating element 112. Embodiments of antenna 104 may be designed with 1-10 shaping elements 114. Shaping elements 114 may be symmetrically or non-symmetrically arranged around radiating element 112. Shaping elements 114 may or may not be identical. In FIG. 3A, each shaping element 114 is elongate, non-linear and comprises a bend or an angled region. In FIG. 3A, each shaping element is electrically connected to the outer conductor of coaxial cable 102 or other transmission line such that each shaping element 114 is located substantially distal to the distal end of the transmission line 102 (in zone Z2). The distal end of radiating element 112 and/or shaping elements 114 may have a sharp or penetrating tip. In one embodiment, shaping elements 114 are a retractable claw structure that extends from ablation device 100. In one embodiment, the design of radiating element 112 is similar to a 14 mm long monopole antenna. In FIG. 3A, shaping elements 114 shape and enhance the electromagnetic field in the volume between radiating element 112 and shaping elements 114. This creates a large, volumetric lesion between radiating element 112 and shaping elements 114. The volumetric lesion will be substantially confined to the extent of shaping elements 114 as seen from FIGS. 3B and 3C. Further, shaping elements 114 reduce the leakage current that will otherwise be induced on the outer wall of the outer conductor of coaxial cable 102 or other transmission line. It should be noted that there is no direct electrical conduction between radiating element 112 and shaping elements 114.

When microwave energy is delivered through a transmission line to antenna 104 in FIG. 3A, a first microwave field is emitted by radiating element 112. The first microwave field interacts with shaping elements 114. This interaction induces a leakage current on shaping elements 114. The leakage current in turn creates a second microwave field. The first microwave field and the second microwave field together combine to produce a unique shaped microwave field of antenna 104 that is clinically more useful that the unshaped microwave field generated by an antenna 104 comprising only radiating element 112. Thus the original microwave field is redistributed by the design of shaping elements 114. Shaping elements 114 alone are not capable of functioning as an antenna; rather shaping elements 114 shape or redistribute the electromagnetic or microwave field emitted by radiating element 112 to produce a shaped microwave field that is clinically more useful. Further, the combination of radiating element 112 and shaping elements 114 improves the power deposition of antenna 104.

Figure 3B:
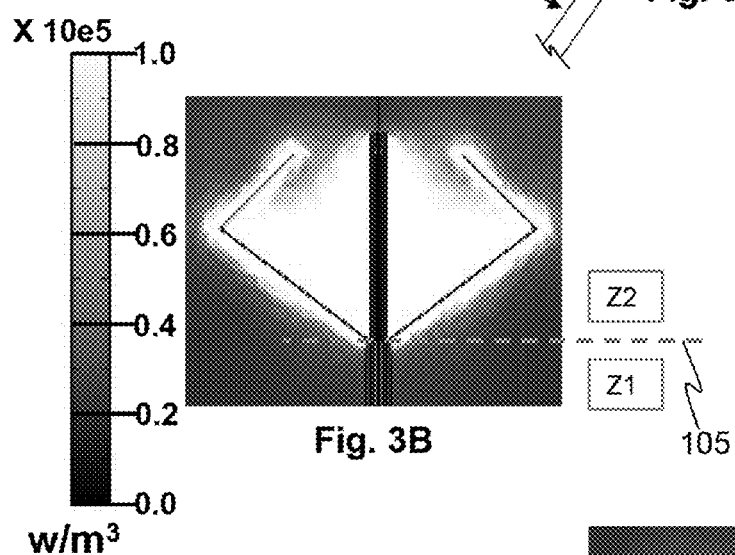
FIGS. 3B and 3C show a side view and a top view of a simulated SAR profile of an embodiment of the antenna of FIG. 3A.

The microwave effect of shaping elements 114 can be seen by comparing FIG. 2H to FIG. 3B. In absence of shaping elements 114, antenna 104 in FIG. 3A acts as a monopole antenna similar to that shown in FIG. 2H. Thus FIG. 2H shows a first unshaped field that is not shaped by shaping elements 114. When the antenna 104 comprises shaping elements 114 as shown in FIG. 3A, the antenna generates a shaped microwave field as shown in FIG. 3B.

In an embodiment of a minimally invasive procedure, antenna 104 is inserted into the patient's body through small puncture wounds in the skin. Thereafter, antenna 104 is deployed such that the volume enclosed by the claw-like shaping elements 114 encloses the target tissue. For example, for cancer treatment, the target tissue is a tumor or a tissue with cancer cells. The degree of deployment of antenna 104 may be adjusted to suit different target tissue sizes (e.g. different tumor sizes). In one such embodiment, one or more pull wires or tethers are attached to shaping elements 114 to control the position of shaping elements 114. In another embodiment, shaping elements 114 are pre-shaped and are made of a material with shape memory properties such as Nitinol. Shaping elements 114 are retracted inside a catheter or a tubular structure in a collapsed configuration before inserting into the tissue. A low-profile catheter or a tubular structure is preferably used to reduce the trauma to healthy tissues during the insertion procedure. Once a portion of the catheter or tubular structure is inserted inside the target tissue, shaping elements 114 and radiating element 112 are deployed. Shaping elements 114 are deployed to their un-collapsed, preset shape by extending them from the catheter or tubular structure. Even though antenna 104 of FIG. 3A can be used for a variety of procedures, it is especially suited for ablating solid tumors such as those found in cancer (e.g. liver and lung cancer) and benign tumors (e.g. uterine fibroids).

Figure 3C:
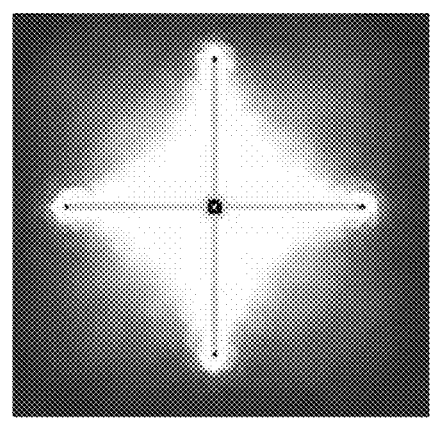

FIGS. 3B and 3C show a side view and a top view of a simulated SAR profile of an embodiment of the antenna of FIG. 3A. The SAR profile was simulated at 2.45 GHz using the COMSOL Multiphysics package to simulate an ablation in the liver. FIGS. 3B and 3C illustrate that a volumetric lesion created by antenna 104 will be substantially confined to the extent of shaping elements 114. Also, FIGS. 3B and 3C show that the microwave field volumetrically envelops entire antenna 104.

In the embodiment of FIG. 3B, the nearest conductive path is provided by the conductive shaping elements 114 instead of the shielding element of the distal region of the transmission line 102. The presence of shaping elements 114 has prevented the microwave field from coupling to the distal region of the transmission line 102. Virtually none of the microwave field is located around the distal region of transmission line 102. Further, since a vast majority of the emitted microwave field is deposited in zone Z2, the power deposition of antenna 102 is improved. Virtually no portion of the field is wasted in zone Z1.

Figures 3D, 3E:
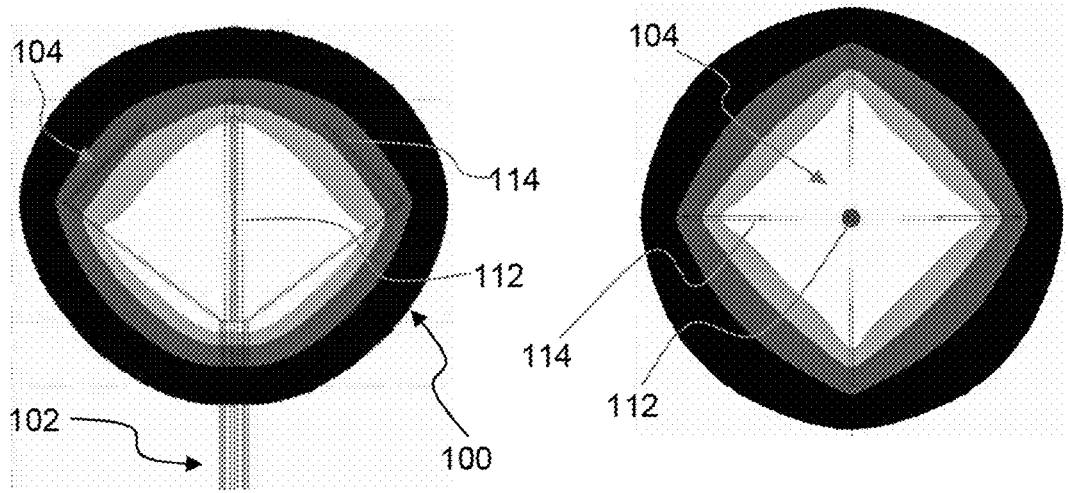
FIGS. 3D and 3E show a side view and a top view of a thermal simulation of an embodiment of the antenna of FIG. 3A.

FIGS. 3D and 3E show a side view and a top view of a thermal simulation of an embodiment of the antenna of FIG. 3A. The outer most surface of the black zone is a 50° C. isosurface with a diameter or width of about 28 mm and longitudinal length of about 22 mm at steady state. Thus, antenna 104 is capable for forming a lesion with a diameter or width of about 28 mm and longitudinal length of about 22 mm. The 50° C. isosurface encloses the 60° C. isosurface (boundary between the black and dark grey zones) which in turn encloses the 70° C. isosurface (boundary between the dark grey and light grey zones) which in turn encloses the 80° C. isosurface (boundary between the light grey and white zones).

Figure 3F:
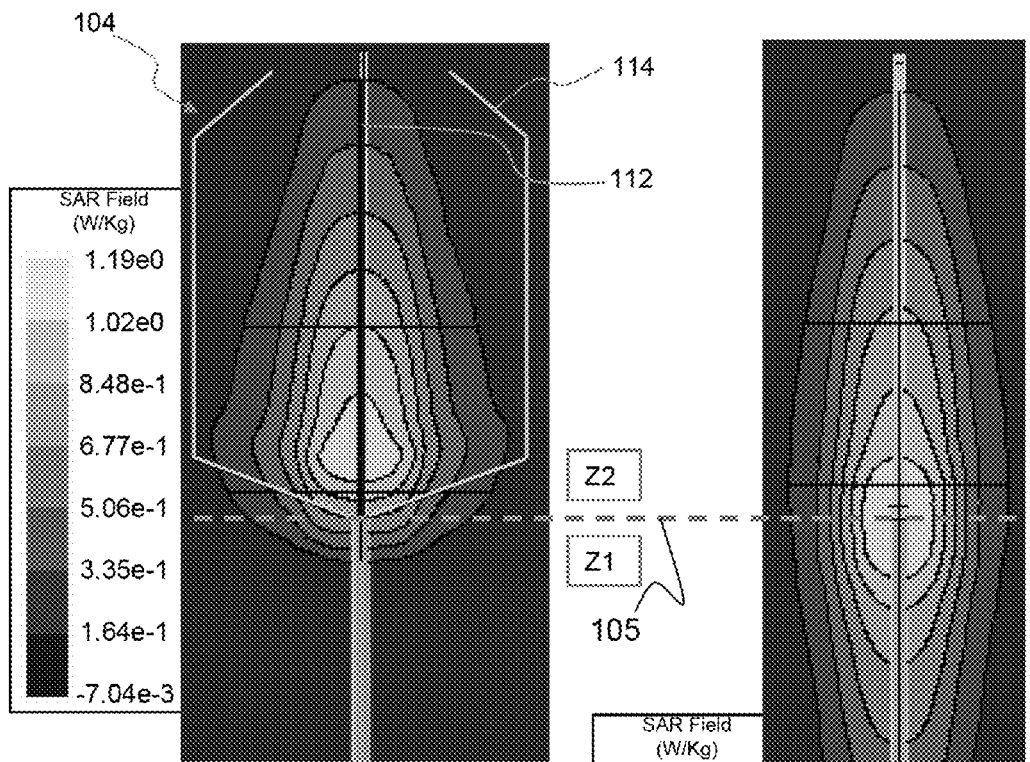
FIGS. 3F and 3G show a side view and a top view of a simulated SAR profile at 0.915 GHz of an embodiment of an antenna similar to the antenna of FIG. 3A.
Figure 3G:
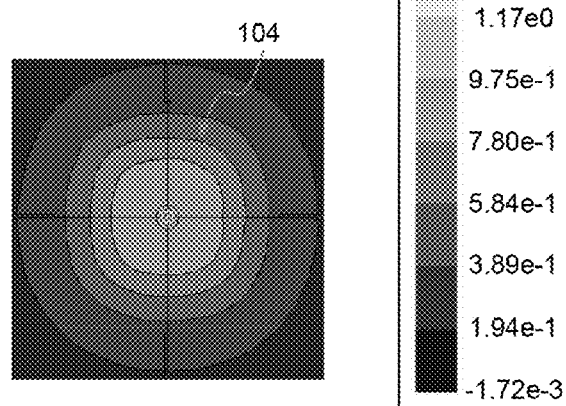

FIGS. 3F and 3G show a side view and a top view of a simulated SAR profile at 0.915 GHz of an embodiment of an antenna similar to the antenna of FIG. 3A. The SAR profile was simulated at 0.915 GHz using the Ansoft HFSS package to simulate an ablation in the liver. Radiating element 112 in FIGS. 3F and 3G is linear and has a length of about a quarter of the effective wavelength. FIGS. 3F and 3G illustrate that the volumetric lesion will be substantially confined to the extent of shaping elements 114.

The antenna 104 shown in FIGS. 3F and 3G comprises a substantially linear radiating element 112 with a plurality of shaping elements 114. The four shaping elements 114 shown in FIGS. 3F and 3G are identical and are arranged symmetrically around radiating element 112. Embodiments of antenna 104 may be designed with 1-10 shaping elements 114 arranged symmetrically or non-symmetrically arranged around radiating element 112. Shaping elements 114 may or may not be identical. In FIGS. 3F and 3G, each shaping element is elongate and comprises two bends or angled regions. Similar to the embodiment in FIG. 3A, each shaping element is electrically connected to the shielding element of the transmission line such as outer conductor of coaxial cable 102. The distal end of radiating element 112 and/or shaping elements 114 may have a sharp or penetrating tip. In one embodiment, shaping elements 114 are a retractable claw structure that extends from ablation device 100. In FIGS. 3F and 3G, shaping elements 114 enhance the electromagnetic field in the space between radiating element 112 and shaping elements 114. This creates a large, volumetric lesion between radiating element 112 and shaping elements 114. The volumetric lesion is substantially confined to the extent of shaping elements 114 as shown in FIGS. 3F and 3G. Further, shaping elements 114 reduce the leakage current that will otherwise be induced on the outer wall of the outer conductor of coaxial cable 102.

In FIGS. 3F and 3G, radiating element 112 comprises an elongate conductor that is about 39+/−5 mm long. The distal end of the elongate conductor may be covered by a metallic tubular cap that is in conductive contact with the elongate conductor. Entire radiating element 112 is covered with a layer of dielectric material such as silicone. Each shaping element 114 comprises a proximal bend and a distal bend. The proximal bend is arranged at a longitudinal distance of about 5 mm from the distal end of the transmission line measured along the length of the radiating element 112. The longitudinal distance between the proximal bend and the distal bend measured along the length of the radiating element 112 is about 29 mm. The longitudinal distance between the distal bend and the distal end of shaping element 114 measured along the length of the radiating element 112 is about 5 mm. Thus the total longitudinal length of each shaping element 114 measured along the length of radiating element 112 is about 39 mm. The maximum diameter of the structure formed by shaping elements 114 is about 30 mm. The use of antenna 104 in FIGS. 3F and 3G is similar to antenna 104 of FIG. 3A.

Figure 3H:
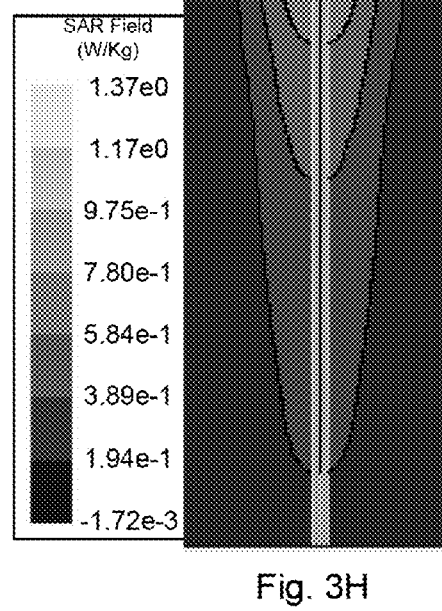
FIG. 3H shows a side view of a simulated SAR profile at 0.915 GHz of an embodiment of an antenna similar to the antenna of FIG. 3F but without shaping elements 114.

FIG. 3H shows a side view of a simulated SAR profile at 0.915 GHz of an embodiment of an antenna similar to the antenna of FIG. 3F but without shaping elements 114. The effect of shaping elements 114 is clear when the SAR profile of FIG. 3F is compared to the SAR profile of FIG. 3H. In the embodiment of FIG. 3F, the nearest conductive path is provided by the conductive shaping elements 114 instead of the shielding element of the distal region of the transmission line 102. The presence of shaping element 114 has prevented the microwave field from coupling to the distal region of the transmission line 102. Virtually none of the microwave field is located around the distal region of transmission line 102. Further, since a vast majority of the emitted microwave field is deposited in zone Z2, the power deposition of antenna 102 is improved. Virtually no portion of the field is wasted in zone Z1.

Figure 3I:
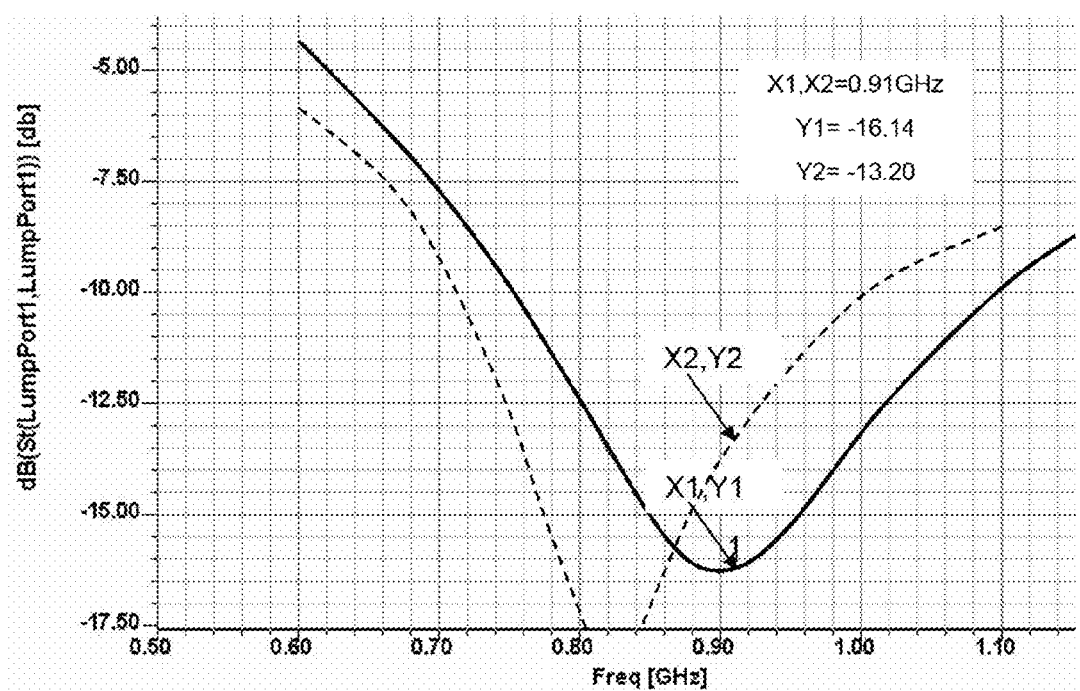
FIG. 3I shows the comparison of the simulated return loss of ablation devices with antennas of FIGS. 3F and 3H.

FIG. 3I shows the comparison of the simulated return loss of ablation devices with antennas of FIGS. 3F and 3H. The simulated return loss shows good matching (about −16.14 dB) at 0.915 GHz with the antenna of FIG. 3F (solid line) that is superior to the matching (about −13.20 dB) at 0.915 GHz with the antenna of FIG. 3H (dashed line). Thus, the design of shaping elements 114 in antenna 104 of FIG. 3F improves the matching and reduces the return loss.

Further, the design of shaping elements 114 in FIG. 3F improves the frequency range over which important performance parameters are acceptable. In FIG. 3I if the solid and dashed lines are compared, at a cutoff of −10 dB, the acceptable frequency range between 0.6 GHz to 1.1 GHz in the embodiment containing shaping element 114 is about 0.35 GHz (spanning from approximately 0.75 GHz to approximately 1.1 GHz). The acceptable frequency range between 0.6 GHz to 1.1 GHz in the comparable embodiment of FIG. 3H without shaping element 114 is only about 0.29 GHz (spanning from approximately 0.71 GHz to approximately 1.0 GHz). Thus in the first case, a larger frequency range (bandwidth) is available over which antenna 104 delivers an acceptable performance. This in turn allows for a design of antenna 104 wherein minor distortions of antenna 104 during typical clinical use or due to minor manufacturing variations do not significantly affect the performance of antenna 104.

Any of the methods and devices disclosed herein may be used to cause therapeutic fibrotic vein occlusion by controlled heating of the vein. The fibrotic vein occlusion may be caused by one or more of endothelial destruction, collagen contraction and vein wall thickening.

Various antennas disclosed herein may be used for the delivery of microwave energy to cause controlled heating of tissue may to treat disorders of anatomical lumens. Examples of such disorders of anatomical lumens include, but are not limited to: BPH, stress urinary incontinence, gastroesophageal reflux disease and fecal incontinence. In one embodiment, a device or method disclosed herein may be used for deeper tissue heating to cause tissue shrinkage for treating conditions such as fecal incontinence, GERD, urinary incontinence, etc. Such deeper heating may be carried out with the device placed within the lumens or other bodily cavities.

In any of the method and device embodiments disclosed herein, one or more shaping elements 114 may be introduced through a separate device or a separate introduction path to shape the microwave energy profile generated by an antenna 104.

Any of the method and device embodiments disclosed herein may be used along with a suitable surface cooling modality. Examples of such cooling modalities include, but are not limited to: inflatable structures inflated with a cooling fluid, gels or other conformable dielectric structures and structures designed to circulate one or more cooling fluids on a surface of antenna 104 and/or the transmission line.

Several embodiments of planar antennas 104 are also included in the scope of the invention. Such planar antennas 104 may be used to ablate or otherwise treat planar or non-planar tissue regions. Such planar antennas 104 may comprise single or multiple splines, curves or loops in a generally planar arrangement. Planar antennas 104 may be used for ablating a surface such as the surface of organs such as liver, stomach, esophagus, a heart chamber, etc. For example, FIG. 4A shows a view of a planar antenna of a microwave ablation device designed for endometrial ablation. In FIG. 4A, microwave ablation device 100 comprises a transmission line (such as a coaxial cable 102) terminating in an antenna 104 at the distal end of the transmission line. In one embodiment, a single microwave signal is fed to antenna 104 through coaxial cable 102. Antenna 104 generates a microwave field. The near field of the microwave field generated by antenna 104 is used for endometrial ablation. In FIG. 4A, antenna 104 comprises a radiating element in the form of an outer loop 112 and a shaping element in the form of a metallic center loop 114. Outer loop 112 and center loop 114 may touch each other when deployed in the anatomy. In one embodiment, outer loop 112 is a continuation of the inner conductor of coaxial cable 102. Center loop 114 shapes or redistributes the microwave field radiated by outer loop 112. It should be noted that there is no direct electrical conduction between outer loop 112 and center loop 114. When microwave energy is delivered through coaxial cable 102 to antenna 104, a first microwave field is emitted by outer loop 112. The first microwave field interacts with center loop 114. This interaction induces a leakage current on center loop 114. The leakage current in turn creates a second microwave field. The first microwave field and the second microwave field together combine to produce a unique shaped microwave field of antenna 104 that is clinically more useful that the unshaped microwave field generated by an antenna 104 comprising only outer loop 112. Thus the original microwave field is redistributed by the design of center loop 114. Center loop 114 alone is not capable of functioning as an antenna; rather center loop 114 shapes or redistributes the electromagnetic or microwave field emitted by outer loop 112 to produce a shaped microwave field that is clinically more useful. Further, the combination of outer loop 112 and center loop 114 improves the power deposition of antenna 104.

In one embodiment, outer loop 112 has no sharp corners. Sharp corners in outer loop 112 may cause the field to concentrate in the vicinity of the sharp corners. In one embodiment, the minimal radius of curvature of a corner in outer loop 112 is at least 0.5 mm. In the embodiment in FIG. 4A, the radius of curvature of corner regions 154 in outer loop 112 is at least 1 mm.

In one embodiment, antenna 104 has a shape that substantially approximates the shape of the body organ to be ablated. For example, antenna in FIG. 4A has a roughly triangular shape that approximates the shape of the uterine cavity and is especially suited for endometrial ablation. The proximal portion of the antenna 104 is directed towards the cervix and corner regions 154 of outer loop 112 are directed towards the fallopian tubes. However, as mentioned before, microwave thermal ablation does not necessarily require perfect contact with all of the target tissue. Thus antenna 104 is able to ablate all or substantially all of the endometrium. The entire endometrium can be ablated in a single ablation by antenna 104 having a single microwave antenna. Thus, repositioning of antenna 104 after an ablation is not needed. This greatly reduces the amount of physician skill needed for the procedure. Further, multiple antennas 104 are not needed in ablation device 100. A single antenna 104 positioned at a single location is able to ablate a therapeutically sufficient amount of the endometrium. This simplifies the design of ablation device 100.

Further, antenna 104 in the working configuration is generally flat and flexible. The plane of outer loop 112 is substantially parallel to the plane of center loop 114. Thus, the uterine walls experience only slight forces from antenna 104. This in turn reduces or eliminates the distension of the uterine wall thereby reducing the discomfort to the patient. This in turn further reduces the anesthesia requirements. Flexible antenna 104 may easily be introduced in a collapsed configuration through a small lumen thereby eliminating or minimizing any cervical dilation. This dramatically reduces the discomfort to the patient consequently significantly reducing the requirement of anesthesia. This antenna 104 design has significant clinical advantages over prior art devices since now the endometrial ablation procedure can be performed in the physician's office under local anesthesia.

Further, flat and flexible antenna 104 in FIG. 4A in its deployed configuration has an atraumatic distal end in which the distal region of antenna 104 is wider than the proximal portion of antenna 104. This reduces the risk of perforation of the uterus. The flexible nature of antenna enables antenna 104 to take the natural shape of the introduction passage instead of distorting the passage. For example, when antenna 104 is introduced trans-cervically into the uterus, antenna 104 may acquire the shape of introduction passage comprising the vagina, cervical canal and uterine cavity instead of distorting one or more of the vagina, cervical canal and uterine cavity.

In one embodiment of a deployed configuration of antenna 104 as shown in FIG. 4A, the length of outer loop 112 measured along the outer loop 112 from the distal end of coaxial cable 102 until the distal end 158 of outer loop 112 is about three quarters of the effective wavelength at the 915 MHz ISM band. The effective wavelength is dependent on the medium surrounding the antenna and the design of an antenna dielectric on the outer loop 112. The design of the antenna dielectric includes features such as the type of dielectric(s) and thickness of the dielectric layer(s). The exact length of the outer loop 112 is determined after tuning the length of outer loop 112 to get good impedance matching. The length of the outer loop 112 in one embodiment is 100+/−15 mm. In one embodiment, the width of deployed outer loop 112 is 40+/−15 mm and the longitudinal length of deployed outer loop 112 measured along the axis of coaxial cable 102 from line 105 till the distal most region of outer loop 112 is 35+/−10 mm. In the embodiment shown in FIG. 4A, an antenna dielectric 116 in the form of a roughly Y-shaped dielectric piece 160 comprising two distal end regions 162 is located roughly at the center of antenna 104. Dielectric piece 160 provides sites for mechanical attachment of various regions of antenna 104 and helps antenna 104 to be deployed from and retracted into an introducing sheath 164. A first distal end region 162 is roughly oriented towards the central axis of antenna 104 and has sites for attachment of distal regions of outer loop 112 and center loop 114 as shown. In one embodiment, the first distal end region 162 has two openings through which distal regions of outer loop 112 and center loop 114 pass. In another embodiment, first distal end region 162 is attached to outer loop 112 and center loop 114 by one or more of: glues or adhesives, mechanical fastening structures, heat shrinkable elements, etc. Distal end 158 of outer loop 112 is mechanically connected to a second distal end region 162 as shown. The mechanical connection may be made by one or more of: glues or adhesives, mechanical fastening structures, heat shrinkable elements, etc. Dielectric piece 160 may be constructed from a material selected from the group consisting of: PEEK, PEBAX, ABS and other relatively stiff polymer materials. An additional function of the dielectric piece 160 is to provide the user with force feedback about the proper position of the device inside a uterus. In one embodiment of a clinical procedure, antenna 104 is inserted in a collapsed, undeployed configuration through introducing sheath 164 into the uterine cavity. Thereafter, antenna 104 is pushed distally relative to introducing sheath 164 to deploy antenna 104 out of the distal end of introducing sheath 164. This causes antenna 104 to attain the deployed configuration as shown in FIG. 4A. Thereafter, antenna 104 is pushed distally such that the distal most region of antenna 104 (first distal end region 162 of dielectric piece 160) pushes against the fundus. The sufficiently stiff dielectric piece 160 causes the user to feel a resistance as soon as the distal most region of antenna 104 pushes against the fundus. This in turn provides the user with a force feedback about the position of antenna 104 against the fundus.

In one embodiment, the proximal portion of outer loop 112 is designed to be stiffer and have greater mechanical strength than the distal portion. This may be achieved by leaving original dielectric material 110 of coaxial cable 102 on the proximal portion of outer loop 112. In an alternate embodiment, this is achieved by coating the proximal portion of outer loop 112 by a layer of antenna dielectric.

In the embodiment shown in FIG. 4A, the cross sectional shape of outer loop 112 is not uniform along the entire length of outer loop 112. In this embodiment, the proximal portion of outer loop 112 is a continuation of the inner conductor of coaxial cable 102. This portion has a substantially circular cross section. A middle portion of outer loop 112 has a substantially flattened or oval or rectangular cross section. The middle portion may be oriented generally perpendicular to the distal region of coaxial cable 102 in the deployed configuration as shown in FIG. 4A. The middle portion of outer loop 112 is mechanically designed to bend in a plane after deployment in the anatomy. This in turn ensures that the distal most region of ablation device 100 is atraumatic and flexible enough to conform to the target tissue anatomy. This helps in the proper deployment of outer loop 112 in the uterus. In one embodiment, the middle portion of outer loop 112 is a continuation of inner conductor of coaxial cable 102 and is flattened. In one embodiment, the distal most portion of outer loop 112 is a continuation of inner conductor of coaxial cable 102 and is non-flattened such that it has a circular cross section. In one embodiment, outer loop 112 is made of a length of a Nitinol or stainless steel wire. A distal portion of the wire is deformed (e.g. by flattening) or has material removed (e.g. by grinding, laser machining, EDM, etc.). Thereafter, the wire is plated with a layer of highly conductive materials such as Au or Ag. This wire is used to replace the inner conductor 108 of coaxial cable 102. This assembly is then used to construct microwave device 100. In another embodiment, outer loop 112 is made of a length of a Nitinol or stainless steel wire clad with a layer of highly conductive materials such as Au or Ag. A distal portion of the wire is deformed (e.g. by flattening). This wire is used to replace the inner conductor 108 of coaxial cable 102. This assembly is then used to construct microwave device 100.

One or more outer surfaces of outer loop 112 may be covered with one or more layers of antenna dielectrics 116. One or more outer surfaces of center loop 114 may be covered with one or more layers of antenna dielectrics 116. The thickness and type of antenna dielectric material along the length of outer loop 112 are engineered to optimize the microwave field shape. In one embodiment shown in FIG. 4A, every portion of outer loop 112 is covered with some antenna dielectric material such that no metallic surface of outer loop 112 is exposed to tissue. Thus, in the embodiment of FIG. 4A, outer loop 112 is able to transmit a microwave field into tissue, but unable to conduct electricity to tissue. Thus, in the embodiment of FIG. 4A, there is no electrical conduction and no conductive path between outer loop 112 and center loop 114 even though outer loop 112 and center loop 114 may physically touch each other when deployed in the anatomy. Examples of dielectric materials that can be used as antenna dielectrics in one or more embodiments disclosed herein include, but are not limited to EPTFE, PTFE, FEP and other fluoropolymers, Silicone, Air, PEEK, polyimides, cyanoacrylates, polyolefins, epoxy, natural or artificial rubbers and combinations thereof. The antenna dielectric 116 on the proximal portion of outer loop 112 may be a continuation of the dielectric 110 of coaxial cable 102. There may be an additional layer of a stiffer antenna dielectric 116 over this layer of antenna dielectric 116.

In the embodiment of FIG. 4A, the dielectric on outer loop 112 is a blend of polyolefins. In another embodiment, the dielectric on the middle portion of outer loop 112 is a silicone layer with or without impregnated air or a silicone tube enclosing a layer of air. In another embodiment, the dielectric on the distal most portion of outer loop 112 is a silicone layer with or without impregnated air or a silicone tube enclosing a layer of air or EPTFE. The thickness of an antenna dielectric on any portion of outer loop 112 may vary or be constant along the length of outer loop 112. Further, the cross section of an antenna dielectric on any portion of outer loop 112 may not be symmetric. The various configurations of the antenna dielectric are designed to achieve the desired ablation profile as well as achieve the desired impedance matching or power efficiency. In an alternate embodiment, entire outer loop 112 is covered with silicone dielectric. In one such embodiment, the layer of silicone used to coat the distal most portion of outer loop 112 may be thinner than the layer of silicone used to coat the middle portion of outer loop 112. The thinner silicone dielectric compensates for the lower field strength that normally exists at the distal most portion of a radiating element such as outer loop in FIG. 4A. Thus, the microwave field is made more uniform along the length of outer loop 112.

In one device embodiment, outer loop 112 is made of a metallic material and the circumference of the metallic material of the distal region of outer loop 112 is more than the circumference of the metallic material of the middle portion of outer loop 112. This causes the silicone dielectric to stretch more at the distal portion than at the middle portion of outer loop 112. This in turn generates a thinner layer of antenna dielectric at the distal portion of outer loop 112 than at the middle portion of outer loop 112. In another embodiment, entire outer loop 112 is made from a single length of metallic wire of a uniform cross section. In this embodiment, a tubular piece of silicone dielectric of varying thickness is used to cover outer loop 112. The tubular silicone dielectric is used to cover the distal and middle portions of outer loop 112 such that the layer of silicone dielectric is thinner near the distal portion and thicker near the middle portion of outer loop 112.

In FIG. 4A, the shape of outer loop 112 is different from the shape of center loop 114. Further, in FIG. 4A, outer loop 112 and center loop 114 are substantially planar and the plane of outer loop 112 is substantially parallel to the plane of center loop 114. Further, in FIG. 4A, both outer loop 112 and center loop 114 are non-linear.

In the embodiments wherein the transmission line is a coaxial cable, two proximal ends of center loop 114 are in electrical contact with two regions on the outer conductor 106. In one embodiment, the two proximal ends of center loop 114 are electrically connected to diametrically opposite regions on or near the distal end of outer conductor 106 such that center loop 114 is located distal to the distal end of the transmission line 102 (in zone Z2). In one embodiment, the two proximal ends of center loop 114 are soldered to the distal end of outer conductor 106. In another embodiment, the two proximal ends of center loop 114 are laser welded to the distal end of outer conductor 106. The two proximal ends of center loop 114 may be connected to the distal end of outer conductor 106 in various configurations including, but not limited to lap joint and butt joint. In an alternate embodiment, at least one of the two proximal ends of center loop 114 is not connected to the distal end of outer conductor 106. For example, at least one of the two proximal ends of center loop 114 may be electrically connected to a region of outer conductor 106 that is proximal to the distal end of outer conductor 106. In one embodiment, the two proximal ends of center loop 114 are tucked inside the distal end of outer jacket 118. In this embodiment, the proximal end of dielectric piece 160 pushes against the two proximal ends of center loop 114. Thus the two proximal ends of center loop 114 are held in place by friction. A transmission line jacket 166 may be located over a part of or the entire portion of the transmission line e.g. a coaxial cable that connects to antenna 104. As shown in FIG. 4A, the distal end of transmission line jacket 166 is located near the two proximal ends of center loop 114. Transmission line jacket 166 may be made of sufficiently stiff materials including, but not limited to: PEEK, PEBAX, FEP, fluoropolymers, polyurethanes, etc. that increase the stiffness of the transmission line. This in turn allows the user to obtain force feedback during the procedure as described earlier. Also, the stiff transmission line jacket 166 facilitates the pushing or pulling or turning of the device during a procedure by a user.

In a method embodiment, when ablation device 100 is used for endometrial ablation, antenna 104 of FIG. 4A generates a microwave field that is more concentrated in the center of the uterus and is less concentrated towards the cornual regions and towards the cervix. Thus, the depth of ablation generated by antenna 104 is deeper in the center of the uterus and is less deep towards the cornual regions and towards the cervix. Such a profile is clinically desired for improved safety and efficacy. In one embodiment, the ablation profile is shaped to ablate a majority of the basalis layer of the uterine endometrium. In one embodiment, center loop 114 is made of a round or flat wire. Examples of wires that can be used to make center loop 114 are wires made of Ag or Au plated or clad or drawn filled tubes of Nitinol or stainless steel. In one embodiment, the wire used to make center loop 114 has a cross sectional profile of about 0.025"×about 0.007". In one embodiment, center loop 114 is made of a wire of round cross section with two flattened ends and a central flattened portion. In one such embodiment, center loop 114 is made of an Ag or Au clad Nitinol or stainless steel wire with a circular cross sectional profile and a diameter of 0.01"+/−0.005". The wire has two flattened ends and a central flattened portion with a cross sectional dimensions of 0.011"+/−0.005" by 0.007"+/−0.003". Such loop shaped shaping elements 114 do not act as a shield for the microwave field. This non-shielding action is visible in the SAR pattern in FIG. 4B. In FIG. 4B, there is no sharp drop in the microwave field intensity past center loop 114. In the embodiment of FIG. 4A, center loop 114 is roughly oval in shape. Two proximal ends of center loop 114 are electrically attached to two diametrically opposite regions of the outer conductor of coaxial cable 102. In the embodiment of FIG. 4A, the width of center loop 114 is 20+/−10 mm and the longitudinal length of deployed center loop 114 measured along the axis of coaxial cable 102 from line 105 till the distal most region of center loop 114 is 33+/−10 mm. When ablation device 100 is used for endometrial ablation, outer loop 112 and center loop 114 both contact the endometrial tissue surface.

Center loop 114 may be mechanically independent from outer loop 112 or may be mechanically attached to outer loop 112. In the embodiment shown in FIG. 4A, center loop 114 and outer loop 112 are both mechanically connected to dielectric piece 160. In an alternate embodiment, a portion of center loop 114 passes through the interior of outer loop 112. In an alternate embodiment, a portion of center loop 114 is mechanically connected to outer loop 112. This may be done for example, by using an adhesive to connect a portion of center loop 114 to outer loop 112. In an alternate embodiment, one or more portions of center loop 114 are mechanically connected to one or more portions of outer loop 112 by one or more flexible attachments.

Parts of center loop 114 may or may not be covered by one or more layers of antenna dielectric materials 116. In the embodiment of FIG. 4A, one or more or all metallic surfaces of center loop 114 are exposed to the device environment.

Portions of outer loop 112 and center loop 114 may be made from one or more of lengths of metals such as copper, Nitinol, aluminum, silver or any other conductive metals or alloys. One or more portions of outer loop 112 and center loop 114 may also be made from a metallized fabric or plastics.

FIGS. 4B and 4C show the front and side views respectively of the SAR profile generated by an antenna with a center loop similar to the antenna of FIG. 4A. In the embodiment shown in FIGS. 4B and 4C, center loop 114 is not covered with any antenna dielectric 116. Thus the metallic surface of center loop 114 is exposed to the surrounding. Outer loop 112 and center loop 114 may physically touch each other when deployed in the anatomy as shown in FIG. 4C. In FIG. 4B, the microwave field is shaped such that the field intensity towards the center of antenna 104 is higher than the field intensity towards the corners of antenna 104. This in turn means that the ablation at the center of antenna 104 will be deeper than the ablation at the corners of antenna 104. Also, the microwave field is shaped such that it is wider distally and narrower proximally. Such a microwave field shape is clinically desirable for endometrial ablation. Also, FIGS. 4B and 4C show that the microwave field volumetrically envelops entire antenna 104. Also, FIGS. 4B and 4C show that the microwave field is substantially bilaterally symmetric. FIGS. 4E and 4F show the front and side views of the SAR profile generated by antenna 104 of FIG. 4A without center loop 114. The microwave effect of shaping element 114 in FIG. 4B can be seen by comparing FIG. 4B to FIG. 4E. FIG. 4E shows a first unshaped field that is not shaped by shaping element 114. When the antenna 104 comprises a shaping element 114 as shown in FIG. 4B, the antenna generates a shaped microwave field as shown in FIG. 4B.

It should be noted that in FIGS. 4B and 4C, the shaped microwave field is more uniformly distributed over a wider area of the endometrium than in FIG. 4E. In FIG. 4E, the unshaped microwave field is more concentrated over the distal region of coaxial cable 102. A more uniformly distributed, shaped microwave field such as in FIGS. 4B and 4C is clinically desirable for endometrial ablation. Further when antenna 104 of FIG. 4B is used for endometrial ablation, the microwave field is distributed over a wider area of the endometrium that the microwave field generated by antenna 104 of FIG. 4E. This can be seen by comparing the SAR profile distal to the distal end of coaxial cable 102 in FIGS. 4B and 4C to the SAR profile distal to the distal end of coaxial cable 102 in FIG. 4E. Further, in FIG. 4E, a portion of the unshaped microwave field extends to a significant distance proximal to the distal end of coaxial cable 102. In FIGS. 4B and 4C, an insignificant portion of the microwave field extends proximally to the distal end of coaxial cable 102. In the embodiment of FIGS. 4A and 4B, the nearest conductive path is provided by the conductive shaping element 114 instead of the shielding element of the distal region of the transmission line 102.

The presence of shaping element 114 has prevented the microwave field from coupling to the distal region of the transmission line 102. Virtually none of the microwave field is located around the distal region of transmission line 102. Further, since a vast majority of the emitted microwave field is deposited in zone Z2, the power deposition of antenna 102 is improved. Virtually no portion of the field is wasted in zone Z1. Thus the microwave field profile of FIGS. 4B and 4C is advantageous over the microwave field profile of FIG. 4E since it limits collateral damage to healthy tissue. Thus the presence of center loop 114 shapes the microwave field such that the microwave field is more distributed. In absence of center loop 114, the microwave field interacts with an element of transmission line 102 such as the outer conductor of a coaxial cable. This results in a non-desirable profile of the microwave field e.g. a concentrated field around the distal region of the transmission line 102 as shown in FIG. 4E. This interaction can also cause backward heating of coaxial cable 102 that may lead to collateral damage of healthy tissue. Further, the combination of outer loop 112 and center loop 114 creates a more robust antenna 104 wherein the performance of antenna 104 is less affected by distortions during clinical use. Also, FIGS. 4B and 4C show that the microwave field volumetrically envelops entire antenna 104.

Further, the SAR profile of FIG. 4B demonstrates that the entire uterine endometrium can be ablated in a single ablation. Thus the physician does not need to reposition antenna 104 after a first endometrial ablation. This novel aspect of the device and procedure greatly reduces the amount of time needed for the procedure and also reduces the procedure risks and physician skill requirements. In the embodiments disclosed herein, a combination of direct microwave dielectric heating and thermal conduction through tissue is used to achieve the desired therapeutic effect. The thermal conduction evens out any minor variations in the microwave field and enables the creation of a smooth, uniform ablation. Further, the SAR profile of FIGS. 4B and 4C demonstrates that antenna 104 is capable of ablating an entire volume surrounding antenna 104 not just ablating between the surfaces of outer loop 112 and center loop 114. Further, the SAR profile of FIGS. 4B and 4C demonstrates that antenna 104 is capable of ablating a tissue region without leaving any "gaps" of unablated tissue within that tissue region. Further, the SAR profile of FIGS. 4B and 4C demonstrates that the entire microwave field generated by antenna 104 is used for ablation. The entire microwave field comprises the microwave field around outer loop 112, the microwave field around center loop 114, the microwave field between outer loop 112 and center loop 114 and the field within center loop 114. Further, the SAR profile of FIGS. 4B and 4C demonstrates that the microwave field is located all around outer loop 112 and is not shielded or reflected by center loop 114. Thus center loop 114 does not act as a shield or reflector in the embodiment shown in FIGS. 4B and 4C.

Figure 4D:
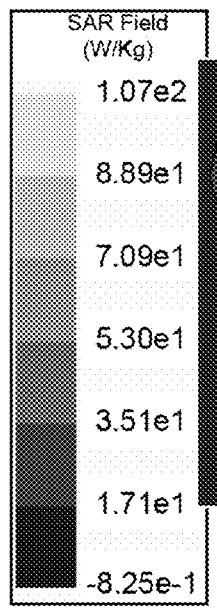
FIG. 4D shows the simulated return loss of an ablation device with the antenna of FIG. 4B compared to the simulated return loss of an ablation device with the antenna of FIG. 4E.
Figure 4D:
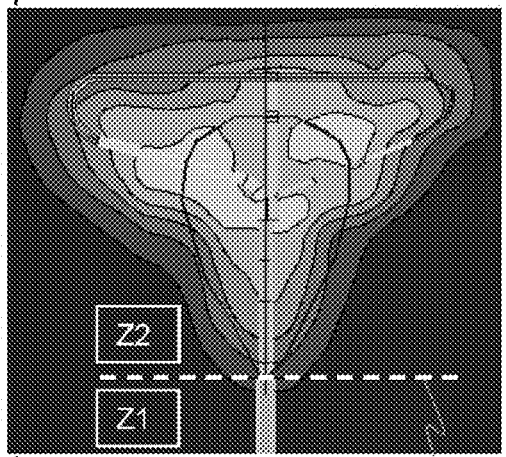
Figure 4D:
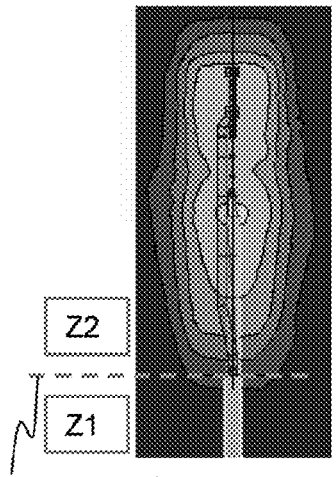
Figure 4D:
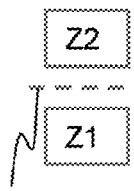
Figure 4D:
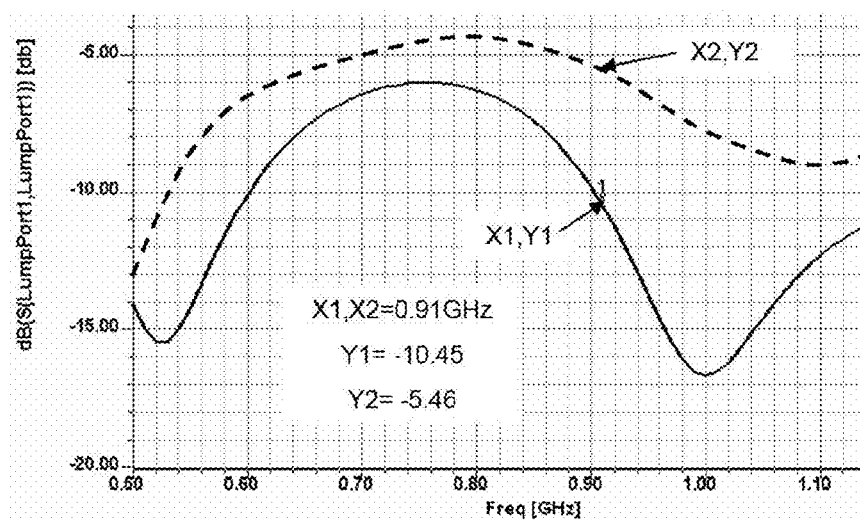
Figure 4E:
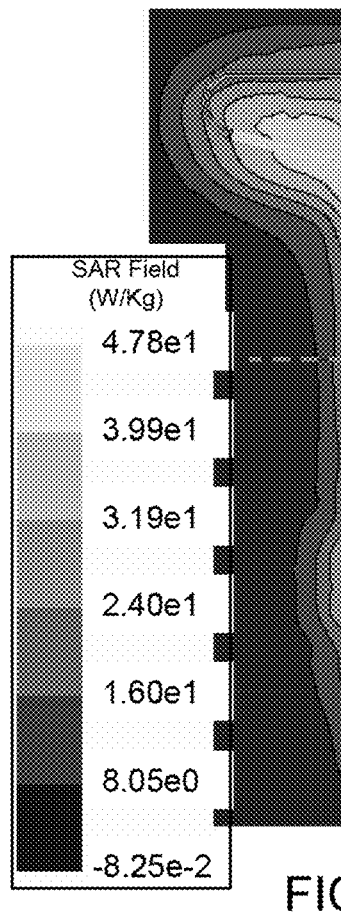
FIGS. 4E and 4F show the front and side views of the SAR profile generated by the antenna of FIG. 4A without a center loop.
Figure 4F:
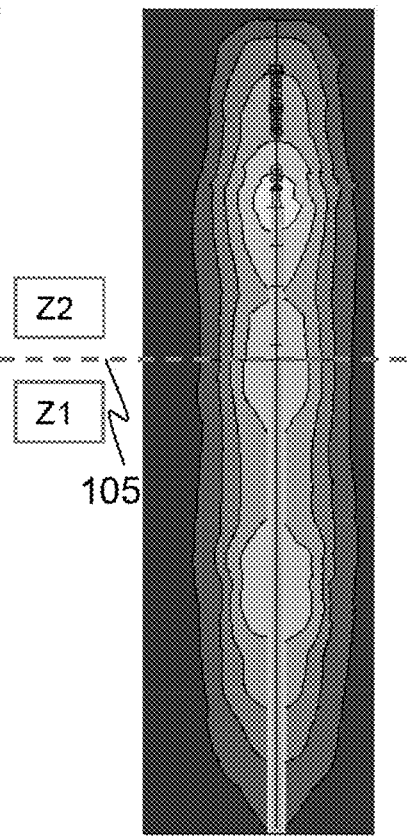

FIG. 4D shows the simulated return loss of an ablation device with antenna 104 of FIG. 4B compared to the simulated return loss of an ablation device with antenna 104 of FIG. 4E. The simulated return loss of an ablation device with antenna 104 of FIG. 4B (solid line) shows good matching (about −10.45 dB) at 915 MHz. The simulated return loss of an ablation device with antenna 104 of FIG. 4E (dashed line) shows a return loss of about −5.46 dB at 915 MHz. Thus, the presence of center loop 114 also improves the matching, reduces the return loss and increases the power efficiency. In the presence of center loop 114, microwave power is delivered more efficiently to the tissue and not wasted as heat generated within ablation device 100.

Shaping element 114 also increases the frequency range (bandwidth) over which antenna 104 delivers an acceptable performance. If the graphs in FIG. 4D are compared, at a cutoff of −10 dB, the acceptable frequency range between 0.5 to 1.0 GHz in the embodiment containing shaping element 114 is about 0.2 GHz (spanning from approximately 0.50 GHz to 0.60 GHz and from 0.90 GHz to 1.0 GHz). The acceptable frequency range between 0.5 to 1.0 GHz in the comparable embodiment of FIG. 4E without shaping element 114 is only about 0.03 GHz (spanning from approximately 0.50 GHz to approximately 0.53 GHz). Thus in the first case, a larger frequency range (bandwidth) is available over which antenna 104 delivers an acceptable performance. This in turn allows for a design of antenna 104 wherein minor distortions of antenna 104 during typical clinical use or due to minor manufacturing variations do not significantly affect the performance of antenna 104.

Any of the microwave antennas 104 disclosed herein may be designed such that a portion of the antenna 104 is shaped by the target region from an insertion configuration to a working configuration capable of carrying out its intended purpose. For example, an antenna 104 similar to that shown in FIG. 4A may be designed such that the antenna 104 achieves the working configuration after antenna 104 is pushed by the uterine fundus and flattened.

Any of the microwave antennas 104 disclosed herein may be designed such that a portion of the antenna 104 is deployable by engaging a mechanical deployment system. The mechanical deployment system may be used to change antenna 104 from an insertion configuration to a working configuration capable of carrying out its intended purpose. One example of such a mechanical deployment system is a system of one or more pullable and releasable pull wires.

Several alternate planar antennas 104 may he designed that comprise anywhere between 1-4 planar radiating elements 112 and 1-6 planar shaping elements 114. The shape of the one or more planar radiating elements 112 and planar shaping elements 114 may be selected from the group consisting of: full or partial loop, linear segments, heart shaped segments, spirals, curved segments, zig-zag segments, etc.

Any of the antennas 104 disclosed herein may comprise one or more mechanisms to ensure proper deployment of antenna 104 in the anatomy. In one such embodiment, the shape memory or super-elastic nature of one or both of one or more radiating elements 112 and one or more shaping elements 114 ensures proper deployment of antenna 104 in the anatomy. In one embodiment, one or both of one or more radiating elements 112 and one or more shaping elements 114 are embedded in a rigid or flexible antenna dielectric 116. Antenna dielectric 116 may be used to fix the relative positions of radiating elements 112 and shaping elements 114 thereby ensuring proper deployment in the anatomy. Such an antenna dielectric 116 may be substantially planar or substantially linear or substantially 3-dimensional. Such antenna dielectrics 116 may be one or more rigid or flexible struts or connection elements connecting one or more radiating elements 112 and one or more shaping elements 114. Such struts or connection elements fix the relative positions of radiating elements 112 and shaping elements 114 thereby ensuring proper deployment of antenna 104 in the anatomy. In one embodiment, a dielectric constraining element mechanically shapes antenna 104 and also shapes the microwave field profile of antenna 104.

In one method embodiment, the duty cycle of microwave power delivery is varied during the course of a procedure. In one method embodiment, the magnitude of microwave power delivered to tissue is varied during the course of a procedure.

Any of the antennas 104 disclosed herein may be used to penetrate through a body tissue to ablate a target. TO facilitate the penetration though tissue, a distal end of any of antenna 104 disclosed herein may be modified (e.g. by having a sharp tip) to facilitate a penetration of tissue. For example, antenna 104 of FIG. 2A may be designed to be sufficiently stiff and have a sharp distal tip to penetrate skin to ablate abdominal and other internal organs.

In one such embodiment, antenna 104 (e.g. antenna 104 of FIG. 2A) is inserted while enclosed inside a sufficiently stiff outer sheath made of a dielectric material.

In another embodiment, antenna 104 has a sufficient mechanical strength to penetrate tissue. The length of ablation device 100 may range from 5 cm to 60 cm. Ablation device 100 may be introduced through a surgical incision such as a laparotomy or a thoracotomy. Ablation device 100 may also be introduced through a surgical instrument port such as a port for laparoscopic or thoracoscopic instruments. Ablation device 100 may be introduced percutaneously by penetrating the skin using a distal penetrating tip and advancing antenna 104 into target tissue. Such percutaneous introduction may be used for example, to ablate liver or lung or uterine tumors with appropriate guidance such as radiological guidance or direct visual or endoscopic guidance. The low profile of antenna 104 enables antenna 104 to be introduced multiple times at different regions in the target tissue sequentially without causing excessive damage to healthy tissue. Multiple ablation devices 100 may also be introduced simultaneously in the target tissue to ablate a larger region of tissue.

To vary the size and/or shape and/or volume of tissue to be treated, relative position and/or the size of one or both of radiating element 112 and shaping element 114 may be changed. Antennas 104 such as shown in FIG. 2A may be inserted in a helical configuration. Such helical shaped antennas 104 may be used to obtain better contact with target tissue. For example, the outer diameter of antenna 104 in FIG. 2A in a helical configuration may be increased to increase the force exerted on the surrounding tissue by antenna 104. In a particular embodiment, a helical antenna 104 is used to heat one or more regions of a target vein for treating venous reflux disease. A helical configuration of antenna 104 may be created by one or more of: introducing antenna 104 in a helical introducing catheter or tube, having a pre-shaped helical antenna 104, twisting a sufficiently rigid device attached to a portion of antenna 104, and pulling or pushing a sufficiently rigid device attached to a portion of antenna 104.

Any of the ablation devices 100 introducing catheter or sheath disclosed herein may comprise a fluid transport lumen. The fluid transport lumen may be used for one or more of evacuating liquids or gases from the anatomy; introducing liquids inside the body such as anesthetics, contrast agents, cauterizing agents, alcohols, thermal cooling agents, a fluid dielectric medium that surrounds antenna 104, drugs (e.g. antibiotics, chemotherapeutics, etc.), liposome encapsulated drugs, saline and flushing solutions; introducing gases inside the body such as carbon dioxide for distending a cavity (e.g. the uterine or peritoneal cavity) or detecting perforation of a cavity, applying suction to collapse a tissue region around the antenna 104, etc. Suction may be applied inside a cavity (e.g. the uterine cavity) to increase the contact of antenna 104 with lining of the cavity.

Any of the devices disclosed herein including any ablation device 100 disclosed herein may comprise a device transport lumen. The device transport lumen may be used for one or more of: introducing one or more elongate diagnostic and/or therapeutic devices in the body, introducing ablation device 100 over a guidewire or other introducing device and introducing an imaging or visualization device.

Any of the devices disclosed herein may comprise a cooling modality to cool one or more regions of the device.

For example, a device may comprise a cooling jacket or another cooling modality to cool one or more of: a surface of the device, a shaft of the device and an antenna of the device.

Any of the devices disclosed herein may comprise one or more of: an impedance measuring modality, a temperature measuring modality and an electrophysiological signal measuring modality.

Any of the antennas 104 disclosed herein may comprise or be used in combination with a microwave shielding or absorbing element. The microwave shielding or absorbing element may shield a majority of or a part of the microwave field emitted by antenna 104. Examples of microwave shielding or absorbing elements include, but are not limited to: inflatable or non-inflatable balloons, hollow structures filled with air or a circulating or non-circulating fluid, metallic wires or meshes, metallic films or other flattened structures, gels or other conformable structures, structures filled or wetted with water, structures designed to circulate one or more fluids on the surface of antenna 104, cooling modalities and mechanical spacers made of dielectric materials.

In one such embodiment, a tubular microwave shielding or absorbing element surrounds a substantially linear antenna 104. The length of the microwave field shape and the resulting lesion length by antenna 104 may be changed by sliding the microwave shielding or absorbing element relative to antenna 104. Such microwave shielding or absorbing elements in combination with an antenna 104 disclosed herein may be used to ablate a local region of tissue (e.g. a part of the uterine endometrium or a vascular endothelium) or to ablate only a single surface of the tissue (e.g. a single surface of the uterine endometrium).

Any antenna 104 disclosed herein may be inserted and/or used under endoscopic (e.g. using hysteroscopy, cystoscopy, endoscopy, laparoscopy, flexible endoscopy, etc.) guidance. Any antenna 104 disclosed herein may be inserted and/or used under ultrasonic guidance. Any antenna 104 disclosed herein may be inserted and/or used under radiological (e.g. X-ray or fluoroscopic) guidance.

Even though a majority of the disclosure uses a coaxial cable as an example of a transmission line, an alternate transmission lines for transmitting microwaves may be used. Examples of such alternate transmission lines for transmitting microwaves include, but are not limited to: waveguides, microstrip lines, strip lines, coplanar waveguides and rectax. In such embodiments, the shaping element(s) 114 may be in electrically connected directly or indirectly to the shielding element of the transmission line. For example, in a strip line, wherein the shielding element is the combination of the two ground planes, shaping element(s) 114 may be electrically connected directly or indirectly to the combination of the two ground planes. For example, in a hollow metallic waveguide, wherein the shielding element is the electrically conducting wall, shaping element(s) 114 may be electrically connected directly or indirectly to the electrically conducting wall.

In one embodiment, microwave reflectometry is used to determine the proper positioning and/or proper deployment of antenna 104.

Several examples or embodiments of the invention have been discussed herein, but various modifications, additions and deletions may be made to those examples and embodiments without departing from the intended spirit and scope of the invention. Thus, any element, component, method step or attribute of one method or device embodiment may be incorporated into or used for another method or device embodiment, unless to do so would render the resulting method or device embodiment unsuitable for its intended use. For example, several embodiments of ablation devices 100 may be created by combining antenna 104 of one embodiment with a device feature of another embodiment unless to do so would render the resulting device embodiment unsuitable for its intended use. Any suitable antenna disclosed herein may be used to perform any of the methods disclosed herein. If the various steps of a method are disclosed in a particular order, the various steps may be carried out in any other order unless doing so would render the method embodiment unsuitable for its intended use. Various reasonable modifications, additions and deletions of the described examples or embodiments are to be considered equivalents of the described examples or embodiments.

The invention claimed is:

1. A microwave energy delivery device for supplying energy from an energy source, the microwave energy delivery device comprising:
    a transmission line having a shielding element that terminates at a distal end of the transmission line;
    a microwave antenna portion located at the distal end of the transmission line and comprising a radiating element and a shaping element; where
    the radiating element is fed by the transmission line to emit a microwave field when energized by the energy source;
    where the shaping element is in electrical contact with the shielding element and is located adjacent to the radiating element such that at least a portion of the shaping element extends along a portion of the radiating element; and
    the shaping element is positioned within and is surrounded by the microwave field to couple the microwave field to the shaping element causing a change to a shape to the microwave field by limiting the microwave field around the microwave antenna portion such that the microwave field is uniform about the radiating element and the shaping element and where the shaping element affects the microwave field by limiting the microwave field to beyond the distal end of the transmission line.

2. The microwave energy delivery device of claim 1, where the transmission line comprises a flexible member.

3. The microwave energy delivery device of claim 1, where the antenna comprises a profile selected from a group consisting of: a linear profile, a non-linear profile, a planar profile, and a 3 dimensional profile.

4. The microwave energy delivery device of claim 1, where the microwave antenna is located at a distal end of the transmission line and the radiating element and the shaping member are located distal to the distal end of the transmission line.

5. The microwave energy delivery device of claim 1, wherein the radiating element comprises a conductor selected from the group consisting of a non-linear conductor, a linear conductor, a helical conductor, and a planar conductor.

6. The microwave energy delivery device of claim 1, wherein the radiating element comprises a conductor having a length that is an odd multiple of one quarter of the effective wavelength and where the wavelength is selected from a group consisting of 433 MHz ISM band, 915 MHz ISM band, 2.45 GHz ISM band and 5.8 GHz ISM band.

7. The microwave energy delivery device of claim 1, wherein the radiating element comprises a continuation portion of a conductor of the transmission line.

8. The microwave energy delivery device of claim 1, where the shaping element is connected to the shielding element at or near the distal end of the transmission line.

9. The microwave energy delivery device of claim 1, where the shaping element comprises a profile selected from the group consisting of a linear profile, a non-linear profile, a planar profile, a 3 dimensional profile.

10. The microwave energy delivery device of claim 1, where the radiating element and shaping element are parallel.

11. The microwave energy delivery device of claim 1, where radiating element is planar and the shaping element is planar and the plane of radiating element is parallel to the plane of shaping member.

12. The microwave energy delivery device of claim 1, where the shaping element is located distal to the distal end of the transmission line.

13. The microwave energy delivery device of claim 1, where the shaping element improves a power efficiency of the antenna.

14. The microwave energy delivery device of claim 1, where the shaping element improves the impedance matching of the device.

15. The microwave energy delivery device of claim 1, where the shaping element improves the bandwidth over which the antenna delivers an acceptable performance.

16. The microwave energy delivery device of claim 1, where the antenna further comprises a dielectric that covers one or both of: radiating element and shaping member and shapes the microwave field by changing the local dielectric environment in the region wherein antenna dielectric is located.

17. The microwave energy delivery device of claim 16, where the antenna dielectric electrically insulates radiating element from the surrounding.

18. The microwave energy delivery device of claim 1, where the microwave antenna generates a microwave field profile selected from the group consisting of: a radially symmetric microwave field profile and a bilaterally symmetric microwave field profile.

19. The microwave energy delivery device of claim 1, wherein the antenna generates a microwave field profile that is wider distally and narrower proximally.

20. The microwave energy delivery device of claim 1, where the microwave field extends volumetrically around the microwave antenna.

21. The microwave energy delivery device of claim 1, where the shaping element affects the microwave field to prevent heating of the distal region of the transmission line.

22. The microwave energy delivery device of claim 1, where the shaping element is in direct or indirect electrical contact with the shielding element.

23. The microwave energy delivery device of claim 1, where the distal region of the transmission line requires no cooling or additional insulation.

24. A microwave energy delivery device comprising:
a transmission line having a shielding element;
a microwave antenna located distally to a terminating end of the shielding element and comprising a radiating element and a shaping element where positioning of the shaping element adjacent to the radiating element reduces a return loss of the antenna;
where the radiating element is fed by the transmission line wherein the radiating element emits a microwave field when an energy supply delivers energy to the transmission line; and
the shaping element in electrical contact with the shielding element wherein the shaping element is positioned within and is surrounded by the microwave field to allow the microwave field emitted by the radiating element to couple to the shaping element and cause a change in shape to the microwave field to reduce coupling of the microwave field with a distal region of the transmission line proximal to the microwave antenna and limit the microwave field about the microwave antenna and where the shaping element affects the microwave field by limiting the microwave field to beyond the terminating end of the shielding element.

25. A microwave energy delivery device comprising:
a transmission line having a shielding element that terminates at a distal end of the transmission line;
a microwave antenna located at the distal end of the transmission line and comprising a radiating element and a shaping element; where
the radiating element is fed by the transmission line wherein the radiating element emits a microwave field when an energy supply delivers energy to the transmission line; and
the shaping element is in electrical contact with the shielding element wherein the shaping element is positioned relative to the radiating element, the shaping element is positioned within and surrounded by the microwave field to improve a power deposition of the microwave antenna by redistributing the microwave field such that the microwave field couples to the shaping element to extend distally from the transmission line and around to the microwave antenna and where the shaping element affects the microwave field by limiting the microwave field to beyond the distal end of the transmission line.

26. A microwave energy delivery device comprising:
a transmission line having a shielding element;
a microwave antenna located distally to a terminating end of the shielding element and comprising a radiating element and a shaping element; where
the radiating element is fed by the transmission line wherein the radiating element emits a microwave field; and
the shaping element is in electrical contact with the shielding element wherein at least
a portion of the shaping element extends along a portion of the radiating element such that the shaping element is positioned within and is surrounded by the microwave field and interacts with the microwave field to establish a conductive path with the microwave field to cause the microwave field to electrically couple to the shaping element and reduces coupling to the distal region of the transmission line such that the microwave field extends around the microwave antenna and where the shaping element affects the microwave field by limiting the microwave field to beyond the terminating end of the shielding element.

* * * * *